United States Patent
Phadtare et al.

(10) Patent No.: US 7,476,526 B2
(45) Date of Patent: Jan. 13, 2009

(54) METHOD OF USING A GENE CONFERRING RESISTANCE TO 4,5-DIHYDROXY-2-CYCLOPENTEN-1-ONE (DHCP) AND IDENTIFYING INHIBITORS OF A POLYPEPTIDE ENCODED BY THE GENE

(75) Inventors: Sangita Phadtare, Highland Park, NJ (US); Kunitoshi Yamanaka, Highland Park, NJ (US); Ikunoshin Kato, Kyoto (JP); Masayori Inouye, Piscataway, NJ (US)

(73) Assignee: Takara Bio Inc. (JP)

( * ) Notice: Subject to any disclaimer, the term of this patent is extended or adjusted under 35 U.S.C. 154(b) by 377 days.

(21) Appl. No.: 11/224,538

(22) Filed: Sep. 12, 2005

(65) Prior Publication Data

US 2007/0166786 A1 Jul. 19, 2007

Related U.S. Application Data

(62) Division of application No. 09/805,681, filed on Mar. 14, 2001, now abandoned.

(60) Provisional application No. 60/228,727, filed on Aug. 29, 2000.

(51) Int. Cl.
| | |
|---|---|
| C12N 9/10 | (2006.01) |
| C12N 15/74 | (2006.01) |
| C12N 15/09 | (2006.01) |
| C12P 21/04 | (2006.01) |
| C07H 21/02 | (2006.01) |
| A61K 49/00 | (2006.01) |

(52) U.S. Cl. .................. 435/193; 435/471; 435/69.2; 435/70.1; 435/91.4; 536/23.1; 424/9.1

(58) Field of Classification Search .................. None
See application file for complete search history.

(56) References Cited

U.S. PATENT DOCUMENTS 6,087,401 A 7/2000 Koyama et al.
6,228,892 B1 5/2001 Tominaga et al.

FOREIGN PATENT DOCUMENTS

WO WO 99/36383 A1 7/1999

OTHER PUBLICATIONS

Lu et al. (1998) Journal of Bacteriology, vol. 180, pp. 5243-5246.*

(Continued)

*Primary Examiner*—Richard Hutson
*Assistant Examiner*—Alexander D Kim
(74) *Attorney, Agent, or Firm*—DLA Piper LLP (US)

(57) ABSTRACT

The invention relates to a gene isolated from *E. coli*, dep, which confers resistance to the antibacterial activity of 4,5-dihydroxy-2-cyclopenten-1-one (DHCP). The invention further relates to the putative protein encoded by dep, which is a hydrophobic, transmembrane efflux protein specific for DHCP. The invention further relates to plasmids containing the dep gene, and to bacterial cells expressing dep. Furthermore, the invention provides applications for use in conferring resistance to antibacterial activity in organisms. The dep gene can be used to identify compounds which inhibit the efflux activity responsible for the resistance to DHCP or to compounds which are functionally equivalent to DHCP.

2 Claims, 8 Drawing Sheets

OTHER PUBLICATIONS

Aiba et al. (1996) DNA Research, vol. 3, pp. 363-377.*

Michael J. Weickert et al., *Optimization of heterologous protein production in Escherichia coli*, Current Opinion in Biotechnology (1996) 7:494-499.

GenBank Accession No. AE00261 created Jan. 22, 1997.

Frederick R. Blattner et al., *The Complete Genome Sequence of Escherichia coli K-12*, Science, vol. 277 Sep. 5, 1997, pp. 1453-1462.

Sangita Phadtare et al., *Antibacterial Activity of 4,5-Dihydroxy-2-cyclopentan-1-one (DHCP) and Cloning of a Gene Conferring DHCP Resistance in Escherichia coli*, Journal of Molecular Microbiology, vol. 3, 2001, pp. 461-465, abstract.

* cited by examiner

Fig. 4

```
Dep   385 CVANS~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
Cmr   384 PALDTVPP~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
CmrA  384 SVQETVPA~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
Cml   386 APADATR~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
Cmx   388 AEAN~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~~
CmlV  409 PGHVVARSRGAGGTTPSEPARGKATSSC~~~~~~~~~~~~~~~~~~~~~~~~~~~~~~~~~~~~~~~~~~~~~~~~~~~~~~~~~~~~~~~~~~~~~~~~~~~~~~~
BcR   372 ......MIW...SIAFCATS..SILFCLYASRPKKR~~~~~~~~~~~~~~~~~~~~~~~~~~~~~~~~~~~~~~~~~~~~~~~~~~~~~~~~~~~~~~~~~~~~~~~
Bmr3  354 ...DTARVW..LTVFMM.ISGFGVGFNFSLL.P..AASMNDLEPRFR.GTANSTNSFLRSFGMTLGVTIFGTVQTNVFTNKLNDAFSGMK.G..SAGSGA.AQNIGDPQE
YjcC  366 ...HTKPI...IAVIMMALCG.G.GFGFFLS.PNQRALMSS.APTTRSGAASGVLGISRILGQTTGATL...VAFCLYLSSDHGAEIALRIGIFIAFAGLYGQFVAFAE.
Tet   421 EVDQSTYLYSNLLLLFSGIIVISWLVTLNLYKHSQRDF~~~~~~~~~~~~~~~~~~~~~~~~~~~~~~~~~~~~~~~~~~~~~~~~~~~~~~~~~~~~~~~~~~~~~~

Dep   390 ~~~~~~~~~~~~~~~~~~~~~~~~~~~~~~~~~~~~~~~~~~~~~~~~~~~~~~~~~~~~~~~~~~~~~~
Cmr   392 ~~~~~~~~~~~~~~~~~~~~~~~~~~~~~~~~~~~~~~~~~~~~~~~~~~~~~~~~~~~~~~~~~~~~~~
CmrA  392 ~~~~~~~~~~~~~~~~~~~~~~~~~~~~~~~~~~~~~~~~~~~~~~~~~~~~~~~~~~~~~~~~~~~~~~
Cml   393 ~~~~~~~~~~~~~~~~~~~~~~~~~~~~~~~~~~~~~~~~~~~~~~~~~~~~~~~~~~~~~~~~~~~~~~
Cmx   392 ~~~~~~~~~~~~~~~~~~~~~~~~~~~~~~~~~~~~~~~~~~~~~~~~~~~~~~~~~~~~~~~~~~~~~~
CmlV  437 ~~~~~~~~~~~~~~~~~~~~~~~~~~~~~~~~~~~~~~~~~~~~~~~~~~~~~~~~~~~~~~~~~~~~~~
BcR   397 ~~~~~~~~~~~~~~~~~~~~~~~~~~~~~~~~~~~~~~~~~~~~~~~~~~~~~~~~~~~~~~~~~~~~~~
Bmr3  450 IFQAGTRSQIPDAILNRIIDAMSSSITY.VFLLALIPIVLAAVTILFMGKARVKTTAEMTKKAN
YjcC  462 ..KADFKKK.P..LLVRLYSRIKNVPSYLIF~~~~~~~~~~~~~~~~~~~~~~~~~~~~~~~~~~~~~~
Tet   459 ~~~~~~~~~~~~~~~~~~~~~~~~~~~~~~~~~~~~~~~~~~~~~~~~~~~~~~~~~~~~~~~~~~~~~~
```

```
4381 gccagccact cagaaggaac acgcacggta tagctgaccg cttccagctg gcgatgcagc
4441 tcctgtgccg catcaacaac actaccatta cgcgctaccg cagcgctaaa ttcgagtgaa
4501 tattctgacc acatagtctg cctgcaaaat ttttgaaacc agtcatcaaa tattaccgtt
4561 tcacaacact aatttcactc cctacacttt gcggcggtgt ttaattgaga gatttagaga
4621 atatacatgc aacctgggaa aagattttta gtctggctgg cgggtttgag cgtactcggt
4681 tttctggcaa ccgatatgta tctgcctgct ttcgccgtca tacaggccga cctgcaaacg
4741 cctgcgtctg ctgtcagtgc cagccttagt ctgttccttg ccggttttgc cgcagcccag
4801 cttctgtggg ggccgctctc cgaccgttat ggtcgtaaac cggtattatt aatcggcctg
4861 acaattttg cgttaggtag tctggggatg ctgtgggtag aaaacgccgc tacgctgctg
4921 gtattgcgtt ttgtacaggc tgtgggtgtc tgcgccgcgg cggttatctg gcaagcatta
4981 gtgacagatt attatccttc acagaaagtt aaccgtattt ttgcggccat catgccgctg
5041 gtgggtctat ctccggcact ggctcctctg ttaggaagct ggctgctggt ccattttcc
5101 tggcaggcga ttttcgccac cctgtttgcc attaccgtgg tgctgattct gcctattttc
5161 tggctcaaac ccacgacgaa ggcccgtaac aatagtcagg atggtctgac ctttaccgac
5221 ctgctacgtt ctaaaaccta tcgcggcaac gtgctgatat acgcagcctg ttcagccagt
5281 ttttttgcat ggctgaccgg ttcaccgttc atccttagtg aaatgggcta cagcccggca
5341 gttattggtt taagttatgt cccgcaaact atcgcgtttc tgattggtgg ttatggctgt
5401 cgcgccgcgc tgcagaaatg gcaaggcaag cagttattac cgtggttgct ggtgctgttt
5461 gctgtcagcg tcattgcgac ctgggctgcg ggcttcatta gccatgtgtc gctggtcgaa
5521 atcctgatcc cattctgtgt gatggcgatt gccaatggcg cgatctaccc tattgttgtc
5581 gcccaggcgc tgcgtccctt cccacacgca actggtcgcg ccgcagcgtt gcagaacact
5641 cttcaactgg gtctgtgctt cctcgcaagt ctggtagttt cctggctgat cagtatcagc
5701 acgccattgc tcaccaccac cagcgtgatg ttatcaacag taatgctggt cgcgctgggt
5761 tacatgatgc aacgttgtga agaagttggc tgccagaatc atggcaatgc cgaagtcgct
5821 catagcgaat cacactgatc tatatcgata tacttatacc taggctgcta acaaaatttt
5881 gttgtatgat tgaaattagc ggcctatact aatttcgagt tgttaaagct acgataaata
5941 ttatgttttt acggggacag gatcgttccc gactcactat ggatagtcat ttcggcaagg
6001 gttcctcctt tccctctgtt ctacgtcgga ttatagactc gcggttttt ctgcgagatt
6061 tctcacaaag cccaaaaagc gtctacgctg ttttaaggtt ctgatcaccg accagtgatg
6121 gagaaactat gagttcatcg tgtatagaag aagtcagtgt accggatgac aactggtacc
6181 gtatcgccaa cgaattactt agccgtgccg gtatagccat taacggttct gccccggcgg
6241 atattcgtgt gaaaaacccc gattttttta aacgcgttct gcaagaaggc tctttggggt
6301 taggcgaaag ttatatggat ggctggtggg aatgtgaccg actggatatg tttttagca
6361 aagtcttacg cgcaggtctc gagaaccaac tcccccatca tttcaaagac adgctgcgta
6421 ttgccggcgc tcgtctcttc aatctgcaga gtaaaaaacg tgcctggata gtcggcaaag
6481 agcattacga tttgggtaat gacttgttca acggttgcct gccctctgta cgccagattg
6541 cctgcgctta ctgaaagat gccgataatc tggaatctgc ccagcaggcg aagctcaaaa
6601 tgatttgtga aaaattgcag ttaaaaccag ggatgcgcgt actggatatt ggctgcggct
6661 ggggcggact ggcacactac atggcatcta attatgacgt aagcgtggtg ggcgtcacca
6721 tttctgccga acagcaaaaa atggctcagg aacgctgtga aggcatggat gtcaccattt
6781 tgctgcaaga ttatcgtgac ctgaacgacc agtttgatcg tattgtttct gtggggatgt
6841 tcgagcacgt cggaccgaaa aattacgata cctatttgc ggtggtggat cgtaatctga
6901 aaccggaagg catattcctg ctccatacta tcggttcgaa aaaaacggat ctgaatgttg
6961 atccctggat taataaatat attttttcga acggttgcct gccctctgta cgccagattg
7021 ctcagtccag cgaaccccac tttgtgatgg aagactggca taacttcggt gctgattacg
7081 atactacgtt gatggcgtgg tatgaacgat tcctcgccgc atggccagaa attgcggata
7141 actatagtga acgctttaaa cgaatgttta cctattatct gaatgcctgt gcaggtgctt
7201 tccgcgcccg tgatattcag ctctggcagg tgtgttctc agcggtgtt gaaaacggcc
7261 ttcgagtggc tcgctaaagg ctattctatc gccccctctc cggggcgat ttcagatcag
7321 gcttctgtgc ctggttgatt catggcattt tctcgtgccg ccagcacacg ttctaccgta
7381 tctaccactg cctgagtttg tggatcgatt tcaatgttga cgcgtgcgcc aagtttttc
7441 ttcccaagag tcgtgcgttc cagtgtttcc ggaattaaat ggacgcaaaa acgcgttggc
7501 gtgacttcgc cgacggtcag gctaatacg tcgatgccaa taaatccttt gtacagaata
7561 tatttcatca actgactatc ctggacttta aaccagatct ggcgattatt ttctgaggct
7621 aatattttcg ccacttcagc agtggtcata atatgacctg acattaagtg tccgccaatt
7681 tcatcactga atttcgcgc acgctcaacg tttacccaat ccccacttt taaatcgcca
7741 agattggtaa tgcgtaacgt ttcttcatc aggtcaaaac tgacatggtt gccgttaatt
7801 tccgtcacgg tcaggcagca accgttatgc gccacggaag caccggttc caggccgtcc
7861 agcatgtggt cgggtaactc caccacatgc gtacgaaaat ttggtttctc gtcaatcgac
7921 accagttttg cggtgccctg tacaatcccc gtaaacatac ttacaactcc tgaaatcagt
7981 taagacattc tgttcagcac aatagcaggt ggaaaacgcc cttaccagtg aagggtaag
8041 aatggctatt ttttcactgg agaattaata aatcctcgct acaatagact gaatttcccc
8101 tgcttcttct ctctgctgcc cattcaggcg gctttttagt ctctcatata actacaaata
8161 aaaggtgttc acgtgcagaa gtatatcagt gaagcgcgtc tgttattagc attagcaatc
8221 ccggtgactc tcgcgcaaat cgcccaaact gcgatgggtt ttgtcagtac cgtgatggcg
```

FIG. 6

```
       [atgc aacctgggaa aagattttta gtctggctgg cgggtttgag cgtactcggt
4681 tttctggcaa ccgatatgta tctgcctgct ttcgccgcca tacaggccga] cctgcaaacg
4741 cctgcgtctg ctgtcagtgc cagccttagt ctgttccttg ccggttttgc cgcagcccag
4801 cttctgtggg ggccgctctc cgaccgttat ggtcgtaaac cggtattatt aatcggcctg
4861 acaattttg cgttaggtag tctggggatg ctgtgggtag aaaacgccgc tacgctgctg
4921 gtattgcgtt ttgtacaggc tgtgggtgtc tgcgccgcgg cggttatctg gcaagcatta
4981 gtgacagatt attatccttc acagaaagtt aaccgtattt ttgcggccat catgccgctg
5041 gtgggtctat ctccggcact ggctcctctg ttaggaagct ggctgctggt ccatttttcc
5101 tggcaggcga ttttcgccac cctgtttgcc attaccgtgg tgctgattct gcctattttc
5161 tggatcaaac ccacgacgaa ggcccgtaac aatagtcagg atggtctgac ctttaccgac
5221 ctgctacgtt ctaaaaccta tcgcggcaac gtgctgatat acgcagcctg ttcagccagt
5281 tttttgcat ggctgaccgg ttcaccgttc atccttagtg aaatgggcta cagcccggca
5341 gttattggtt taagttatgt cccgcaaact atgcgtttc tgattggtgg ttatggctgt
5401 cgcgccgcgc tgcagaaatg gcaaggcaag cagttattac cgtggttgct ggtgctgttt
5461 gctgtcagcg tcattgcgac ctgggctgcg ggcttcatta gccatgtgtc gctggtcgaa
5521 atcctgatcc cattctgtgt gatggcgatt gccaatggcg cgatctaccc tattgttgtc
5581 gcccaggcgc tgcgtccctt cccacacgca actggtcgcg ccgcagcgtt gcagaacact
5641 cttcaactgg gtctgtgctt cctcgcaagt ctggtagttt cctggctgat cagtatcagc
5701 acgccattgc tcaccaccac cagcgtgatg ttatcaacag taatgctggt cgcgctgggt
5761 tacatgatgc aacgttgtga agaagttggc tgccagaatc atggcaatgc cgaagtcgct
5821 catagcgaat cacactga
```

FIG.1

SEQUENCE LISTING

```
<160> NUMBER OF SEQ ID NOS: 12

<210> SEQ ID NO 1
<211> LENGTH: 3900
<212> TYPE: DNA
<213> ORGANISM: Escherichia coli

<400> SEQUENCE: 1
gccagccact cttccagctg acgcacggta tagctgaccg cagaaggaac gcgatgcagc      60
tcctgtgccg cagcgctaaa actaccatta cgcgctaccg catcaacaac ttcgagtgaa     120
tattctgacc acatagtctg cctgcaaaat ttttgaaacc agtcatcaaa tattaccgtt     180
```

-continued

| | |
|---|---|
| tcacaacact aatttcactc cctacactt gcggcggtgt ttaattgaga gatttagaga | 240 |
| atatacatgc aacctgggaa aagattttta gtctggctgg cgggtttgag cgtactcggt | 300 |
| tttctggcaa ccgatatgta tctgcctgct ttcgccgcca tacaggccga cctgcaaacg | 360 |
| cctgcgtctg ctgtcagtgc cagccttagt ctgttccttg ccggttttgc cgcagcccag | 420 |
| cttctgtggg ggccgctctc cgaccgttat ggtcgtaaac cggtattatt aatcggcctg | 480 |
| acaattttg cgttaggtag tctggggatg ctgtgggtag aaaacgccgc tacgctgctg | 540 |
| gtattgcgtt ttgtacaggc tgtgggtgtc tcgccgcgg cggttatctg gcaagcatta | 600 |
| gtgacagatt attatccttc acagaaagtt aaccgtattt ttgcggccat catgccgctg | 660 |
| gtgggtctat ctccggcact ggctcctctg ttaggaagct ggctgctggt ccattttcc | 720 |
| tggcaggcga ttttcgccac cctgtttgcc attaccgtgg tgctgattct gcctatttc | 780 |
| tggctcaaac ccacgacgaa ggcccgtaac aatagtcagg atggtctgac ctttaccgac | 840 |
| ctgctacgtt ctaaaaccta tcgcggcaac gtgctgatat acgcagcctg ttcagccagt | 900 |
| ttttttgcat ggctgaccgg ttcaccgttc atccttagtg aaatgggcta cagcccggca | 960 |
| gttattggtt taagttatgt cccgcaaact atcgcgtttc tgattggtgg ttatggctgt | 1020 |
| cgcgccgcgc tgcagaaatg gcaaggcaag cagttattac cgtggttgct ggtgctgttt | 1080 |
| gctgtcagcg tcattgcgac ctgggctgcg ggcttcatta gccatgtgtc gctggtcgaa | 1140 |
| atcctgatcc cattctgtgt gatggcgatt gccaatggcg cgatctaccc tattgttgtc | 1200 |
| gcccaggcgc tgcgtccctt cccacacgca actggtcgcg ccgcagcgtt gcagaacact | 1260 |
| cttcaactgg gtctgtgctt cctcgcaagt ctggtagttt cctggctgat cagtatcagc | 1320 |
| acgccattgc tcaccaccac cagcgtgatg ttatcaacag taatgctggt cgcgctgggt | 1380 |
| tacatgatgc aacgttgtga agaagttggc tgccagaatc atggcaatgc cgaagtcgct | 1440 |
| catagcgaat cacactgacc tatatcgata tacttatact taggctgcta acaaaatttt | 1500 |
| gttgtatgat tgaaattagc ggcctatact aatttcgagt tgttaaagct acgataaata | 1560 |
| ttatgttttt acggggacag gatcgttccc gactcactat ggatagtcat ttcggcaagg | 1620 |
| gttcctcctt tccctctgtt ctacgtcgga ttatagactc gcggtttttt ctgcgagatt | 1680 |
| tctcacaaag cccaaaaagc gtctacgctg ttttaaggtt ctgatcaccg accagtgatg | 1740 |
| gagaaactat gagttcatcg tgtatagaag aagtcagtgt accggatgac aactggtacc | 1800 |
| gtatcgccaa cgaattactt agccgtgccg gtatagccat taacggttct gccccggcgg | 1860 |
| atattcgtgt gaaaaaccccc gattttttta aacgcgttct gcaagaaggc tctttggggt | 1920 |
| taggcgaaag ttatatggat ggctggtggg aatgtgaccg actggatatg ttttttagca | 1980 |
| aagtcttacg cgcaggtctc gagaaccaac tcccccatca tttcaaagac acgctgcgta | 2040 |
| ttgccggcgc tcgtctcttc aatctgcaga gtaaaaaacg tgcctggata gtcggcaaag | 2100 |
| agcattacga tttgggtaat gacttgttca gccgcatgct tgatcccttc atgcaatatt | 2160 |
| cctgcgctta ctggaaagat gccgataatc tggaatctgc ccagcaggcg aagctcaaaa | 2220 |
| tgatttgtga aaaattgcag ttaaaaccag ggatgcgcgt actggatatt ggctgcggct | 2280 |
| ggggcggact ggcacactac atggcatcta attatgacgt aagcgtggtg ggcgtcacca | 2340 |
| tttctgccga acagcaaaaa atggctcagg aacgctgtga aggcctggat gtcaccattt | 2400 |
| tgctgcaaga ttatcgtgac ctgaacgacc agtttgatcg tattgtttct gtggggatgt | 2460 |
| tcgagcacgt cggaccgaaa aattacgata cctattttgc ggtggtggat cgtaatttga | 2520 |

```
aaccggaagg catattcctg ctccatacta tcggttcgaa aaaaaccgat ctgaatgttg   2580
atccctggat taataaatat attttttccga acggttgcct gccctctgta cgccagattg   2640
ctcagtccag cgaaccccac tttgtgatgg aagactggca taacttcggt gctgattacg   2700
atactacgtt gatggcgtgg tatgaacgat tcctcgccgc atggccagaa attgcggata   2760
actatagtga acgctttaaa cgaatgttta cctattatct gaatgcctgt gcaggtgctt   2820
tccgcgcccg tgatattcag ctctggcagg tcgtgttctc acgcggtgtt gaaaacggcc   2880
ttcgagtggc tcgctaaagg ctattctatc gcccctctc cggggggcgat ttcagatcag   2940 gcttctgtgc ctggttgatt catggcattt tctcgtgccg ccagcacacg ttctaccgta   3000
tctaccactg cctgagtttg tggatcgatt tcaatgttga cgcgtgcgcc aagttttttc   3060
ttcccaagag tcgtgcgttc cagtgttttcc ggaattaaat ggacgcaaaa acgcgttggc   3120
gtgacttcgc cgacggtcag gctaataccg tcgatgccaa taaatccttt gtacagaata   3180
tatttcatca actgactatc ctggactttta aaccagatct ggcgattatt ttctgaggtt   3240
aatattttcg ccacttcagc agtggtcata atatgacctg acattaagtg tccgccaatt   3300
tcatcactga atttcgccgc acgctcaacg tttacccaat cccccacttt taaatcgcca   3360
agattggtaa tgcgtaacgt ttctttcatc aggtcaaaac tgacatggtt gccgttaatt   3420
tccgtcacgg tcaggcagca accgttatgc gccacgaag caccggtttc caggccgtcc   3480
agcatgtggt cgggtaactc caccacatgc gtacgaaaat ttggtttctc gtcaatcgac   3540
accagttttg cggtgccctg tacaatcccc gtaaacatac ttacaactcc tgaaatcagt   3600
taagacattc tgttcagcac aatagcaggt ggaaaacgcc cttaccagtg aagggtaag   3660 aatggctatt ttttcactgg agaattaata aatcctcgct acaatagact gaatttcccc   3720
tgcttcttct ttttgctgcc cattcaggcg gcttttttagt ctctcatata actacaaata   3780
aaaggtgttc acgtgcagaa gtatatcagt gaagcgcgtc tgttattagc attagcaatc   3840 cggtgattc tcgcgcaaat cgcccaaact gcgatgggtt ttgtcagtac cgtgatggcg   3900

<210> SEQ ID NO 2
<211> LENGTH: 1212
<212> TYPE: DNA
<213> ORGANISM: Escherichia coli

<400> SEQUENCE: 2
atgcaacctg ggaaaagatt tttagtctgg ctggcgggtt tgagcgtact cggttttctg     60
gcaaccgata tgtatctgcc tgctttcgcc gccatacagg ccgacctgca aacgcctgcg    120
tctgctgtca gtgccagcct tagtctgttc cttgccggtt ttgccgcagc ccagcttctg    180
tgggggccgc tctccgaccg ttatggtcgt aaaccggtat tattaatcgg cctgacaatt    240
tttgcgttag gtagtctggg gatgctgtgg gtagaaaacg ccgctacgct gctggtattg    300
cgttttgtac aggctgtggg tgtctgcgcc gcggcggtta tctggcaagc attagtgaca    360
gattattatc cttcacagaa agttaaccgt attttttgcgg ccatcatgcc gctggtgggt    420
ctatctccgg cactggctcc tctgttagga agctggctgc tggtccattt ttcctggcag    480
gcgattttcg ccaccctgtt tgccattacc gtggtgctga ttctgcctat tttctggctc    540
aaacccacga cgaaggcccg taacaatagt caggatggtc tgacctttac cgacctgcta    600
cgttctaaaa cctatcgcgg caacgtgctg atatacgcag cctgttcagc cagtttttt    660 gcatggctga ccggttcacc gttcatcctt agtgaaatgg gctacagccc ggcagttatt    720
ggtttaagtt atgtcccgca aactatcgcg tttctgattg gtggttatgg ctgtcgcgcc    780
```

```
gcgctgcaga aatggcaagg caagcagtta ttaccgtggt tgctggtgct gtttgctgtc      840
agcgtcattg cgacctgggc tgcgggcttc attagccatg tgtcgctggt cgaaatcctg      900
atcccattct gtgtgatggc gattgccaat ggcgcgatct accctattgt tgtcgcccag      960
gcgctgcgtc ccttcccaca cgcaactggt cgcgccgcag cgttgcagaa cactcttcaa     1020
ctgggtctgt gcttcctcgc aagtctggta gtttcctggc tgatcagtat cagcacgcca     1080
ttgctcacca ccaccagcgt gatgttatca acagtaatgc tggtcgcgct gggttacatg     1140
atgcaacgtt gtgaagaagt tggctgccag aatcatggca atgccgaagt cgctcatagc     1200
gaatcacact ga                                                         1212
```

<210> SEQ ID NO 3
<211> LENGTH: 389
<212> TYPE: PRT
<213> ORGANISM: Escherichia coli

<400> SEQUENCE: 3

```
Met Lys Ile Asn Tyr Pro Leu Ala Leu Ala Ile Gly Ala Phe Gly
  1               5                  10                  15

Ile Gly Thr Thr Glu Phe Ser Pro Met Gly Leu Pro Val Ile Ala
                 20                  25                  30

Arg Gly Val Asp Val Ser Ile Pro Ala Ala Gly Met Leu Ile Ser Ala
                 35                  40                  45

Tyr Ala Val Gly Val Met Val Gly Ala Pro Leu Met Thr Leu Leu Leu
     50                  55                  60

Ser His Arg Ala Arg Arg Ser Ala Leu Ile Phe Leu Met Ala Ile Phe
 65                  70                  75                  80

Thr Leu Gly Asn Val Leu Ser Ala Ile Ala Pro Asp Tyr Met Thr Leu
                 85                  90                  95

Met Leu Ser Arg Ile Leu Thr Ser Leu Asn His Gly Ala Phe Phe Gly
                100                 105                 110

Leu Gly Ser Val Val Ala Ala Ser Val Val Pro Lys His Lys Gln Ala
                115                 120                 125

Ser Ala Val Ala Thr Met Phe Met Gly Leu Thr Leu Ala Asn Ile Gly
     130                 135                 140

Gly Val Pro Ala Ala Thr Trp Leu Gly Glu Thr Ile Gly Trp Arg Met
145                 150                 155                 160

Ser Phe Leu Ala Thr Ala Gly Leu Gly Val Ile Ser Met Val Ser Leu
                165                 170                 175

Phe Phe Ser Leu Pro Lys Gly Gly Ala Gly Ala Arg Pro Glu Val Lys
                180                 185                 190

Lys Glu Leu Ala Val Leu Met Arg Pro Gln Val Leu Ser Ala Leu Leu
                195                 200                 205

Thr Thr Val Leu Gly Ala Gly Ala Met Phe Thr Leu Tyr Thr Tyr Ile
     210                 215                 220

Ser Pro Val Leu Gln Ser Ile Thr His Ala Thr Pro Val Phe Val Thr
225                 230                 235                 240

Ala Met Leu Val Leu Ile Gly Val Gly Phe Ser Ile Gly Asn Tyr Leu
                245                 250                 255

Gly Gly Lys Leu Ala Asp Arg Ser Val Asn Gly Thr Leu Lys Gly Phe
                260                 265                 270

Leu Leu Leu Leu Met Val Ile Met Leu Ala Ile Pro Phe Leu Ala Arg
                275                 280                 285
```

```
Asn Glu Phe Gly Ala Ala Ile Ser Met Val Val Trp Gly Ala Ala Thr
    290                 295                 300

Phe Ala Val Val Pro Pro Leu Gln Met Arg Val Met Arg Val Ala Ser
305                 310                 315                 320

Glu Ala Pro Gly Leu Ser Ser Ser Val Asn Ile Gly Ala Phe Asn Leu
                325                 330                 335

Gly Asn Ala Leu Gly Ala Ala Ala Gly Gly Ala Val Ile Ser Ala Gly
                340                 345                 350

Leu Gly Tyr Ser Phe Val Pro Val Met Gly Ala Ile Val Ala Gly Leu
            355                 360                 365

Ala Leu Leu Leu Val Phe Met Ser Ala Arg Lys Gln Pro Glu Thr Val
    370                 375                 380

Cys Val Ala Asn Ser
385

<210> SEQ ID NO 4
<211> LENGTH: 391
<212> TYPE: PRT
<213> ORGANISM: Rhodococcus fascians

<400> SEQUENCE: 4

Met Pro Phe Ala Ile Tyr Val Leu Gly Ile Ala Val Phe Ala Gln Gly
1               5                   10                  15

Thr Ser Glu Phe Met Leu Ser Gly Leu Ile Pro Asp Met Ala Gln Asp
            20                  25                  30

Leu Gln Val Ser Val Pro Thr Ala Gly Leu Leu Thr Ser Ala Phe Ala
        35                  40                  45

Ile Gly Met Ile Ile Gly Ala Pro Leu Met Ala Ile Val Ser Met Arg
    50                  55                  60

Trp Gln Arg Arg Ala Leu Leu Thr Phe Leu Ile Thr Phe Met Val
65                  70                  75                  80

Val His Val Ile Gly Ala Leu Thr Asp Ser Phe Gly Val Leu Leu Val
                85                  90                  95

Thr Arg Ile Val Gly Ala Leu Ala Asn Ala Gly Phe Leu Ala Val Ala
            100                 105                 110

Leu Gly Ala Ala Met Ser Met Val Pro Ala Asp Met Lys Gly Arg Ala
        115                 120                 125

Thr Ser Val Leu Leu Gly Gly Val Ile Ile Ala Cys Val Val Gly Val
    130                 135                 140

Pro Gly Gly Ala Leu Leu Gly Glu Leu Trp Gly Trp Arg Ala Ser Phe
145                 150                 155                 160

Trp Glu Val Val Leu Ile Ser Ala Pro Ala Val Ala Ala Ile Met Ala
                165                 170                 175

Ser Thr Pro Ala Asp Ser Pro Thr Asp Ser Val Pro Asn Ala Thr Arg
            180                 185                 190

Glu Leu Ser Ser Leu Arg Gln Arg Lys Leu Gln Leu Ile Leu Val Leu
        195                 200                 205

Gly Ala Leu Ile Asn Gly Ala Thr Phe Cys Ser Phe Thr Tyr Leu Ala
    210                 215                 220

Pro Thr Leu Thr Asp Val Ala Gly Phe Asp Ser Arg Trp Ile Pro Leu
225                 230                 235                 240

Leu Leu Gly Leu Phe Gly Leu Gly Ser Phe Ile Gly Val Ser Val Gly
                245                 250                 255

Gly Arg Leu Ala Asp Thr Arg Pro Phe Gln Leu Leu Val Ala Gly Ser
            260                 265                 270
```

```
Ala Ala Leu Leu Val Gly Trp Ile Val Phe Ala Ile Thr Ala Ser His
        275                 280                 285

Pro Val Val Thr Leu Val Met Leu Phe Val Gln Gly Thr Leu Ser Phe
        290                 295                 300

Ala Val Gly Ser Thr Leu Ile Ser Arg Val Leu Tyr Val Ala Asp Gly
305                 310                 315                 320

Ala Pro Thr Leu Gly Gly Ser Phe Ala Thr Ala Phe Asn Val Gly
            325                 330                 335

Ala Ala Leu Gly Pro Ala Leu Gly Val Ala Ile Gly Ile Gly Met
            340                 345                 350

Gly Tyr Arg Ala Pro Leu Trp Thr Ser Ala Ala Leu Val Ala Leu Ala
        355                 360                 365

Ile Val Ile Gly Ala Ala Thr Trp Thr Arg Trp Arg Glu Pro Arg Pro
        370                 375                 380

Ala Leu Asp Thr Val Pro Pro
385                 390
```

<210> SEQ ID NO 5
<211> LENGTH: 391
<212> TYPE: PRT
<213> ORGANISM: Rhodococcus erythropolis

<400> SEQUENCE: 5

```
Met Pro Phe Ala Ile Tyr Val Leu Gly Leu Ala Val Phe Ala Gln Gly
1               5                   10                  15

Thr Ser Glu Phe Met Leu Ser Gly Leu Ile Pro Asp Met Ala Arg Asp
            20                  25                  30

Leu Gly Val Ser Val Pro Ala Ala Gly Leu Leu Thr Ser Ala Phe Ala
        35                  40                  45

Val Gly Met Ile Ile Gly Ala Pro Leu Met Ala Ile Ala Ser Met Arg
    50                  55                  60

Trp Pro Arg Arg Arg Ala Leu Leu Thr Phe Leu Ile Thr Phe Met Leu
65                  70                  75                  80

Val His Val Ile Gly Ala Leu Thr Ser Ser Phe Glu Val Leu Leu Val
                85                  90                  95

Thr Arg Ile Val Gly Ala Leu Ala Asn Ala Gly Phe Leu Ala Val Ala
            100                 105                 110

Leu Gly Ala Ala Met Ala Met Val Pro Ala Asp Met Lys Gly Arg Ala
        115                 120                 125

Thr Ser Val Leu Leu Gly Gly Val Ile Ile Ala Cys Val Ala Gly Val
    130                 135                 140

Pro Gly Gly Ala Phe Leu Gly Glu Ile Trp Gly Trp Arg Ala Ala Phe
145                 150                 155                 160

Trp Ala Val Val Ile Ser Ala Pro Ala Val Val Ala Ile Met Phe
                165                 170                 175

Ala Thr Pro Ala Glu Pro Pro Ala Glu Ser Thr Pro Asn Ala Lys Arg
            180                 185                 190

Glu Leu Ser Ser Leu Arg Ser Arg Lys Leu Gln Leu Met Leu Val Leu
        195                 200                 205

Gly Ala Leu Ile Asn Gly Ala Thr Phe Cys Ser Phe Thr Tyr Met Ala
    210                 215                 220

Pro Thr Leu Thr Asp Ile Ser Gly Phe Asp Ser Arg Trp Ile Pro Leu
225                 230                 235                 240

Leu Leu Gly Leu Phe Gly Leu Gly Ser Phe Ile Gly Val Ser Val Gly
```

-continued

```
                    245                 250                 255
Gly Arg Leu Ala Asp Thr Arg Pro Phe Gln Leu Leu Ala Val Gly Ser
            260                 265                 270

Ala Ala Leu Leu Thr Gly Trp Ile Val Phe Ala Leu Thr Ala Ser His
        275                 280                 285

Pro Ala Val Thr Leu Val Met Leu Phe Val Gln Gly Ala Leu Ser Phe
    290                 295                 300

Ala Val Gly Ser Thr Leu Ile Ser Gln Val Leu Tyr Ala Ala Asp Ala
305                 310                 315                 320

Ala Pro Thr Leu Gly Gly Ser Phe Ala Thr Ala Ala Phe Asn Val Gly
            325                 330                 335

Ala Ala Leu Gly Pro Ala Leu Gly Leu Ala Ile Gly Met Gly Leu
        340                 345                 350

Ser Tyr Arg Ala Pro Leu Trp Thr Ser Ala Ala Leu Val Thr Leu Ala
            355                 360                 365

Ile Val Ile Gly Ala Ala Thr Leu Ser Leu Trp Arg Arg Pro Ala Ser
370                 375                 380

Val Gln Glu Thr Val Pro Ala
385                 390
```

<210> SEQ ID NO 6
<211> LENGTH: 392
<212> TYPE: PRT
<213> ORGANISM: Streptomyces lividans

<400> SEQUENCE: 6

```
Met Pro Leu Pro Leu Tyr Leu Leu Ala Val Ala Val Cys Ala Met Gly
1               5                   10                  15

Thr Ser Glu Phe Met Leu Ala Gly Leu Val Pro Asp Ile Ala Ser Asp
                20                  25                  30

Leu Gly Val Thr Val Gly Thr Ala Gly Thr Leu Thr Ser Ala Phe Ala
            35                  40                  45

Thr Gly Met Ile Val Gly Ala Pro Leu Val Ala Ala Leu Ala Arg Thr
        50                  55                  60

Trp Pro Arg Arg Ser Ser Leu Leu Gly Phe Ile Leu Ala Phe Ala Ala
65                  70                  75                  80

Ala His Ala Val Gly Ala Gly Thr Thr Ser Phe Pro Val Leu Val Ala
                85                  90                  95

Cys Arg Val Val Ala Leu Ala Asn Ala Gly Phe Leu Ala Val Ala
            100                 105                 110

Leu Thr Thr Ala Ala Ala Leu Val Pro Ala Asp Lys Gln Gly Arg Ala
        115                 120                 125

Leu Ala Val Leu Leu Ser Gly Thr Val Ala Thr Val Ala Gly Val
130                 135                 140

Pro Gly Gly Ser Leu Leu Gly Thr Trp Leu Gly Trp Arg Ala Thr Phe
145                 150                 155                 160

Trp Ala Val Ala Val Cys Cys Leu Pro Ala Ala Phe Gly Val Leu Lys
                165                 170                 175

Ala Ile Pro Ala Gly Arg Ala Thr Ala Ala Thr Gly Gly Pro Pro
            180                 185                 190

Leu Arg Val Glu Leu Ala Ala Leu Lys Thr Pro Arg Leu Leu Leu Ala
        195                 200                 205

Met Leu Leu Gly Ala Leu Val Asn Ala Ala Thr Phe Ala Ser Phe Thr
210                 215                 220
```

-continued

```
Phe Leu Ala Pro Val Val Thr Asp Thr Ala Gly Leu Gly Asp Leu Trp
225                 230                 235                 240

Ile Ser Val Ala Leu Val Leu Phe Gly Ala Gly Ser Phe Ala Gly Val
            245                 250                 255

Thr Val Ala Gly Arg Leu Ser Asp Arg Arg Pro Ala Gln Val Leu Ala
        260                 265                 270

Val Ala Gly Pro Leu Leu Val Gly Trp Pro Ala Leu Ala Met Leu
    275                 280                 285

Ala Asp Arg Pro Val Ala Leu Leu Thr Leu Val Phe Val Gln Gly Ala
290                 295                 300

Leu Ser Phe Ala Leu Gly Ser Thr Leu Ile Thr Arg Val Leu Tyr Glu
305                 310                 315                 320

Ala Ala Gly Ala Pro Thr Met Ala Gly Ser Tyr Ala Thr Ala Ala Leu
            325                 330                 335

Asn Val Gly Ala Ala Gly Pro Leu Val Ala Thr Thr Leu Gly
        340                 345                 350

His Thr Thr Gly Asn Leu Gly Pro Leu Trp Ala Ser Gly Leu Leu Val
        355                 360                 365

Ala Val Ala Leu Leu Val Ala Phe Pro Phe Arg Thr Val Ile Thr Thr
    370                 375                 380

Ala Ala Pro Ala Asp Ala Thr Arg
385                 390
```

<210> SEQ ID NO 7
<211> LENGTH: 391
<212> TYPE: PRT
<213> ORGANISM: Corynebacterium striatum

<400> SEQUENCE: 7

```
Met Pro Phe Ala Leu Cys Val Leu Ala Leu Ala Val Phe Val Met Gly
1               5                   10                  15

Thr Ser Glu Phe Met Leu Ala Gly Leu Leu Pro Ala Ile Ala Thr Glu
            20                  25                  30

Leu Asp Val Ser Val Gly Thr Ala Gly Leu Leu Thr Ser Ala Phe Ala
        35                  40                  45

Val Gly Met Val Val Gly Ala Pro Val Met Ala Ala Phe Ala Arg Arg
    50                  55                  60

Trp Ser Pro Arg Leu Thr Leu Ile Val Cys Leu Leu Val Phe Ala Gly
65                  70                  75                  80

Ser His Val Ile Gly Ala Met Thr Pro Val Phe Ser Leu Leu Leu Ile
            85                  90                  95

Thr Arg Val Leu Ser Ala Leu Ala Asn Ala Gly Phe Leu Ala Val Ala
        100                 105                 110

Leu Ser Thr Ala Thr Thr Leu Val Pro Ala Asn Gln Lys Gly Arg Ala
    115                 120                 125

Leu Ser Ile Leu Leu Ser Gly Thr Thr Thr Ala Thr Val Val Gly Val
130                 135                 140

Pro Ala Gly Ala Leu Leu Gly Thr Ala Leu Gly Trp Arg Thr Thr Phe
145                 150                 155                 160

Trp Ala Ile Ala Ile Leu Cys Ile Pro Ala Ala Val Gly Val Ile Arg
            165                 170                 175

Gly Val Thr Asn Asn Val Gly Arg Ser Glu Thr Ser Ala Thr Ser Pro
        180                 185                 190

Arg Leu Arg Val Glu Leu Ser Gln Leu Ala Thr Pro Arg Leu Ile Leu
    195                 200                 205
```

```
Ala Met Ala Leu Gly Ala Leu Ile Asn Gly Gly Thr Phe Ala Ala Phe
         210                 215                 220

Thr Phe Leu Ala Pro Ile Val Thr Glu Thr Ala Gly Leu Ala Glu Ala
225                 230                 235                 240

Trp Val Ser Val Ala Leu Val Met Phe Gly Ile Gly Ser Phe Leu Gly
                    245                 250                 255

Val Thr Ile Ala Gly Arg Leu Ser Asp Gln Arg Pro Gly Leu Val Leu
                260                 265                 270

Ala Val Gly Gly Pro Leu Leu Leu Thr Gly Trp Ile Val Leu Ala Val
            275                 280                 285

Val Ala Ser His Pro Val Ala Leu Ile Val Leu Val Leu Val Gln Gly
290                 295                 300

Phe Leu Ser Phe Gly Val Gly Ser Thr Leu Ile Thr Arg Val Leu Tyr
305                 310                 315                 320

Ala Ala Ser Gly Ala Pro Thr Met Gly Gly Ser Tyr Ala Thr Ala Ala
                325                 330                 335

Leu Asn Ile Gly Ala Ala Gly Pro Val Leu Gly Ala Leu Gly Leu
                340                 345                 350

Ala Thr Gly Leu Gly Leu Leu Ala Pro Val Trp Val Ala Ser Val Leu
            355                 360                 365

Thr Ala Ile Ala Leu Val Ile Met Leu Leu Thr Arg Arg Ala Leu Thr
370                 375                 380

Lys Thr Ala Ala Glu Ala Asn
385                 390

<210> SEQ ID NO 8
<211> LENGTH: 436
<212> TYPE: PRT
<213> ORGANISM: Streptomyces venezuelae

<400> SEQUENCE: 8

Met Pro Ser Pro Ser Ala Glu Pro Thr Thr Ser Thr Pro Thr Pro Asp
 1               5                  10                  15

Ala Gly Pro Ala Ala Ser Pro Arg Met Pro Leu Ala Val Tyr Ile Leu
                20                  25                  30

Gly Leu Ser Ala Phe Ala Leu Gly Thr Ser Glu Phe Met Leu Ser Gly
            35                  40                  45

Leu Val Pro Pro Ile Ala Glu Asp Met Asn Val Ser Ile Pro Arg Ala
        50                  55                  60

Gly Leu Leu Ile Ser Ala Phe Ala Ile Gly Met Val Val Gly Ala Pro
65                  70                  75                  80

Leu Leu Ala Val Ala Thr Leu Arg Leu Pro Arg Lys Thr Thr Leu Ile
                85                  90                  95

Ala Leu Ile Thr Val Phe Gly Leu Arg Gln Met Ala Gly Ala Leu Ala
            100                 105                 110

Pro Asn Tyr Ala Val Leu Phe Ala Ser Arg Val Ile Ser Ala Leu Pro
        115                 120                 125

Cys Ala Gly Phe Trp Ala Val Gly Ala Ala Val Ala Ile Ala Met Val
130                 135                 140

Pro Val Gly Ser Arg Ala Arg Ala Leu Ala Val Met Ile Gly Gly Leu
145                 150                 155                 160

Ser Ile Ala Asn Val Leu Arg Val Pro Ala Gly Ala Phe Leu Gly Glu
                165                 170                 175

His Leu Gly Trp Ala Ser Ala Phe Trp Ala Val Gly Leu Ala Ser Ala
```

```
                180             185             190
Ile Ala Leu Val Gly Val Val Thr Arg Ile Pro Arg Ile Pro Leu Pro
            195                 200                 205
Glu Thr Arg Pro Arg Pro Leu Lys Asn Glu Val Ala Ile Tyr Arg Asp
            210                 215                 220
Arg Gln Val Leu Leu Ser Ile Ala Val Thr Ala Leu Ala Ala Gly Gly
225                 230                 235                 240
Val Phe Cys Ala Phe Ser Tyr Leu Ala Pro Leu Leu Thr Asp Val Ser
            245                 250                 255
Gly Leu Asp Glu Ala Trp Val Ser Gly Val Leu Gly Leu Phe Gly Ile
            260                 265                 270
Gly Ala Val Val Gly Thr Thr Ile Gly Arg Val Ala Asp Ala His
            275                 280                 285
Leu Phe Gly Val Leu Leu Thr Gly Ile Ser Ala Ser Thr Val Phe Leu
            290                 295                 300
Val Ala Leu Ala Leu Phe Ala Ser Asn Pro Ala Thr Ile Val Leu
305                 310                 315                 320
Thr Phe Leu Leu Gly Val Ser Ala Phe Tyr Thr Ala Pro Ala Leu Asn
            325                 330                 335
Ala Arg Met Phe Asn Val Ala Gly Ala Ala Pro Thr Leu Ala Gly Ala
            340                 345                 350
Thr Thr Thr Ala Ala Phe Asn Leu Gly Asn Thr Gly Gly Pro Trp Leu
            355                 360                 365
Gly Gly Thr Val Ile Asp Ala Asn Leu Gly Phe Ala Ser Thr Ala Trp
            370                 375                 380
Ala Gly Ala Ala Met Thr Val Leu Gly Leu Gly Ile Ala Ala Leu Ala
385                 390                 395                 400
Leu Arg Leu Thr Lys Arg Pro Ala Pro Gly His Val Val Ala Arg Ser
            405                 410                 415
Arg Gly Ala Gly Gly Thr Thr Pro Ser Glu Pro Ala Arg Gly Lys Ala
            420                 425                 430
Thr Ser Ser Cys
            435

<210> SEQ ID NO 9
<211> LENGTH: 396
<212> TYPE: PRT
<213> ORGANISM: Escherichia coli

<400> SEQUENCE: 9

Met Thr Thr Arg Gln His Ser Ser Phe Ala Ile Val Phe Ile Leu Gly
1               5                  10                  15
Leu Leu Ala Met Leu Met Pro Leu Ser Ile Asp Met Tyr Leu Pro Ala
            20                  25                  30
Leu Pro Val Ile Ser Ala Gln Phe Gly Val Pro Ala Gly Ser Thr Gln
            35                  40                  45
Met Thr Leu Ser Thr Tyr Ile Leu Gly Phe Ala Leu Gly Gln Leu Ile
            50                  55                  60
Tyr Gly Pro Met Ala Asp Ser Phe Gly Arg Lys Pro Val Val Leu Gly
65                  70                  75                  80
Gly Thr Leu Val Phe Ala Ala Ala Val Ala Cys Ala Leu Ala Asn
                85                  90                  95
Thr Ile Asp Gln Leu Ile Val Met Arg Phe Phe His Gly Leu Ala Ala
            100                 105                 110
```

```
Ala Ala Ala Ser Val Val Ile Asn Ala Leu Met Arg Asp Ile Tyr Pro
            115                 120                 125

Lys Glu Glu Phe Ser Arg Met Met Ser Phe Val Met Leu Val Thr Thr
130                 135                 140

Ile Ala Pro Leu Met Ala Pro Ile Val Gly Gly Trp Val Leu Val Trp
145                 150                 155                 160

Leu Ser Trp His Tyr Ile Phe Trp Ile Leu Ala Leu Ala Ala Ile Leu
                165                 170                 175

Ala Ser Ala Met Ile Phe Phe Leu Ile Lys Glu Thr Leu Pro Pro Glu
            180                 185                 190

Arg Arg Gln Pro Phe His Ile Arg Thr Thr Ile Gly Asn Phe Ala Ala
        195                 200                 205

Leu Phe Arg His Lys Arg Val Leu Ser Tyr Met Leu Ala Ser Gly Phe
    210                 215                 220

Ser Phe Ala Gly Met Phe Ser Phe Leu Ser Ala Gly Pro Phe Val Tyr
225                 230                 235                 240

Ile Glu Ile Asn His Val Ala Pro Glu Asn Phe Gly Tyr Tyr Phe Ala
                245                 250                 255

Leu Asn Ile Val Phe Leu Phe Val Met Thr Ile Phe Asn Ser Arg Phe
            260                 265                 270

Val Arg Arg Ile Gly Ala Leu Asn Met Phe Arg Ser Gly Leu Trp Ile
        275                 280                 285

Gln Phe Ile Met Ala Ala Trp Met Val Ile Ser Ala Leu Leu Gly Leu
    290                 295                 300

Gly Phe Trp Ser Leu Val Val Gly Val Ala Ala Phe Val Gly Cys Val
305                 310                 315                 320

Ser Met Val Ser Ser Asn Ala Met Ala Val Ile Leu Asp Glu Phe Pro
                325                 330                 335

His Met Ala Gly Thr Ala Ser Ser Leu Ala Gly Thr Phe Arg Phe Gly
            340                 345                 350

Ile Gly Ala Ile Val Gly Ala Leu Leu Ser Leu Ala Thr Phe Asn Ser
        355                 360                 365

Ala Trp Pro Met Ile Trp Ser Ile Ala Phe Cys Ala Thr Ser Ser Ile
    370                 375                 380

Leu Phe Cys Leu Tyr Ala Ser Arg Pro Lys Lys Arg
385                 390                 395

<210> SEQ ID NO 10
<211> LENGTH: 512
<212> TYPE: PRT
<213> ORGANISM: Bacillus subtilis

<400> SEQUENCE: 10

Met Asp Thr Thr Thr Ala Lys Gln Ala Ser Thr Lys Phe Val Val Leu
  1               5                  10                  15

Gly Leu Leu Leu Gly Ile Leu Met Ser Ala Met Asp Asn Thr Ile Val
                 20                  25                  30

Ala Thr Ala Met Gly Asn Ile Val Ala Asp Leu Gly Ser Phe Asp Lys
             35                  40                  45

Phe Ala Trp Val Thr Ala Ser Tyr Met Val Ala Val Met Ala Gly Met
 50                  55                  60

Pro Ile Tyr Gly Lys Leu Ser Asp Met Tyr Gly Arg Lys Arg Phe Phe
 65                  70                  75                  80

Leu Phe Gly Leu Ile Phe Phe Leu Ile Gly Ser Ala Leu Cys Gly Ile
                 85                  90                  95
```

-continued

```
Ala Gln Thr Met Asn Gln Leu Ile Ile Phe Arg Ala Ile Gln Gly Ile
            100                 105                 110
Gly Gly Gly Ala Leu Leu Pro Ile Ala Phe Thr Ile Ile Phe Asp Leu
        115                 120                 125
Phe Pro Pro Glu Lys Arg Gly Lys Met Ser Gly Met Phe Gly Ala Val
130                 135                 140
Phe Gly Leu Ser Ser Val Leu Gly Pro Leu Leu Gly Ala Ile Ile Thr
145                 150                 155                 160
Asp Ser Ile Ser Trp His Trp Val Phe Tyr Ile Asn Val Pro Ile Gly
                165                 170                 175
Ala Leu Ser Leu Phe Phe Ile Ile Arg Tyr Tyr Lys Glu Ser Leu Glu
            180                 185                 190
His Arg Lys Gln Lys Ile Asp Trp Gly Ala Ile Thr Leu Val Val
        195                 200                 205
Ser Ile Val Cys Leu Met Phe Ala Leu Glu Leu Gly Gly Lys Thr Tyr
    210                 215                 220
Asp Trp Asn Ser Ile Gln Ile Ile Gly Leu Phe Ile Val Phe Ala Val
225                 230                 235                 240
Phe Phe Ile Ala Phe Phe Ile Val Glu Arg Lys Ala Glu Glu Pro Ile
                245                 250                 255
Ile Ser Phe Trp Met Phe Lys Asn Arg Leu Phe Ala Thr Ala Gln Ile
            260                 265                 270
Leu Ala Phe Leu Tyr Gly Gly Thr Phe Ile Ile Leu Ala Val Phe Ile
        275                 280                 285
Pro Ile Phe Val Gln Ala Val Tyr Gly Ser Ser Ala Thr Ser Ala Gly
    290                 295                 300
Phe Ile Leu Thr Pro Met Met Ile Gly Ser Val Ile Gly Ser Met Ile
305                 310                 315                 320
Gly Gly Ile Phe Gln Thr Lys Ala Ser Phe Arg Asn Leu Met Leu Ile
                325                 330                 335
Ser Val Ile Ala Phe Phe Ile Gly Met Leu Leu Ser Asn Met Thr
            340                 345                 350
Pro Asp Thr Ala Arg Val Trp Leu Thr Val Phe Met Met Ile Ser Gly
        355                 360                 365
Phe Gly Val Gly Phe Asn Phe Ser Leu Leu Pro Ala Ala Ser Met Asn
    370                 375                 380
Asp Leu Glu Pro Arg Phe Arg Gly Thr Ala Asn Ser Thr Asn Ser Phe
385                 390                 395                 400
Leu Arg Ser Phe Gly Met Thr Leu Gly Val Thr Ile Phe Gly Thr Val
                405                 410                 415
Gln Thr Asn Val Phe Thr Asn Lys Leu Asn Asp Ala Phe Ser Gly Met
            420                 425                 430
Lys Gly Ser Ala Gly Ser Gly Ala Ala Gln Asn Ile Gly Asp Pro Gln
        435                 440                 445
Glu Ile Phe Gln Ala Gly Thr Arg Ser Gln Ile Pro Asp Ala Ile Leu
    450                 455                 460
Asn Arg Ile Ile Asp Ala Met Ser Ser Ile Thr Tyr Val Phe Leu
465                 470                 475                 480
Leu Ala Leu Ile Pro Ile Val Leu Ala Ala Val Thr Ile Leu Phe Met
                485                 490                 495
Gly Lys Ala Arg Val Lys Thr Thr Ala Glu Met Thr Lys Lys Ala Asn
            500                 505                 510
```

<210> SEQ ID NO 11
<211> LENGTH: 487
<212> TYPE: PRT
<213> ORGANISM: Zymomonas mobilis

<400> SEQUENCE: 11

```
Met Met Pro Asp Asp Gln Lys Asn Gly Gln Ala Asn Phe Ser Asp Val
  1               5                  10                  15

Glu Gly Met Thr Arg Gln Asn Arg Asn Gln Ala Met Gly Ala Ile Ser
             20                  25                  30

Val Ser Val Ala Met Ala Ile Leu Asp Thr Ala Ile Val Asn Thr Ala
         35                  40                  45

Leu Pro Ser Ile Ala Lys Asp Leu Gly Val Gly His Ser Asp Ser Val
     50                  55                  60

Trp Ile Ile Thr Ala Tyr Gln Met Ser Met Val Ala Ala Met Leu Pro
 65                  70                  75                  80

Phe Ala Ala Tyr Gly Asp Leu Lys Gly His Arg Lys Val Phe Leu Thr
                 85                  90                  95

Gly Leu Gly Val Phe Ile Leu Ala Ser Leu Ala Cys Gly Ile Ser Pro
            100                 105                 110

Ser Phe Leu Gly Leu Val Ala Ala Arg Phe Val Gln Gly Ile Gly Ala
        115                 120                 125

Ala Ala Ile Met Ser Ala Asn Thr Ala Leu Val Arg Gln Ile Tyr Pro
    130                 135                 140

Ala Arg Ile Leu Gly Arg Gly Leu Gly Leu Asn Ala Leu Val Met Ala
145                 150                 155                 160

Phe Ser Phe Ala Ala Gly Pro Pro Met Ala Ser Ile Ile Leu Ser Phe
                165                 170                 175

Thr Ser Trp His Trp Leu Phe Leu Ile Asn Val Pro Ile Cys Ile Leu
            180                 185                 190

Ala Phe Phe Leu Ser Trp Gln Lys Leu Pro Lys Glu Asp Lys Gly Lys
        195                 200                 205

Ser Gln Lys Phe Asp Val Val Pro Ala Val Ile Cys Ala Ser Leu Phe
    210                 215                 220

Ala Leu Trp Val His Gly Leu Gly Gln Leu Ala His Gly Ser Met Thr
225                 230                 235                 240

Ser Leu Pro Ile Ile Glu Ala Val Ala Leu Ile Leu Gly Ile Phe
                245                 250                 255

Leu Val Arg Trp Gln Ser Ser His Glu Arg Pro Leu Leu Ala Val Asp
            260                 265                 270

Leu Phe Arg Ile Ser Phe Phe Ser Leu Ser Ala Ile Thr Ala Phe Leu
        275                 280                 285

Ala Phe Ile Val Gln Gly Met Ile Phe Val Ala Met Pro Phe Leu Leu
    290                 295                 300

Gln Gly Lys Leu Gly Phe Asp Val Ile Met Thr Gly Phe Leu Ile Ala
305                 310                 315                 320

Pro Trp Pro Leu Met Gly Ala Phe Leu Ala Pro Ile Ala Gly Arg Leu
                325                 330                 335

Ser Asp Arg Tyr Pro Ala Gly Ile Leu Gly Ile Gly Leu Ala Ile
            340                 345                 350

Leu Gly Leu Gly Ile Gly Val Ile Ser Val Leu Pro Pro His Thr Lys
        355                 360                 365

Pro Ile Ile Ala Val Ile Met Met Ala Leu Cys Gly Gly Gly Phe Gly
    370                 375                 380
```

```
Phe Phe Leu Ser Pro Asn Gln Arg Ala Leu Met Ser Ser Ala Pro Thr
385                 390                 395                 400

Thr Arg Ser Gly Ala Ala Ser Gly Val Leu Gly Ile Ser Arg Ile Leu
            405                 410                 415

Gly Gln Thr Thr Gly Ala Thr Leu Val Ala Phe Cys Leu Tyr Leu Ser
            420                 425                 430

Ser Asp His Gly Ala Glu Ile Ala Leu Arg Ile Gly Ile Phe Ile Ala
        435                 440                 445

Phe Ala Gly Leu Tyr Gly Gln Phe Val Ala Phe Ala Glu Lys Ala Asp
    450                 455                 460

Phe Lys Lys Lys Pro Leu Leu Val Arg Leu Tyr Ser Arg Ile Lys Asn
465                 470                 475                 480

Val Pro Ser Tyr Leu Ile Phe
                485

<210> SEQ ID NO 12
<211> LENGTH: 458
<212> TYPE: PRT
<213> ORGANISM: Staphylococcus hyicus

<400> SEQUENCE: 12

Met Asn Thr Ser Tyr Ser Gln Ser Asn Leu Arg His Asn Gln Ile Leu
1               5                   10                  15

Ile Trp Leu Cys Ile Leu Ser Phe Phe Ser Val Leu Asn Glu Met Val
            20                  25                  30

Leu Asn Val Ser Leu Pro Asp Ile Ala Asn Asp Phe Asn Lys Pro Pro
        35                  40                  45

Ala Ser Thr Asn Trp Val Asn Thr Ala Phe Met Leu Thr Phe Ser Ile
    50                  55                  60

Gly Thr Ala Val Tyr Gly Lys Leu Ser Asp Gln Leu Gly Ile Lys Arg
65                  70                  75                  80

Leu Leu Leu Phe Gly Ile Ile Asn Cys Phe Gly Ser Val Ile Gly
            85                  90                  95

Phe Val Gly His Ser Phe Phe Ser Leu Leu Ile Met Ala Arg Phe Ile
            100                 105                 110

Gln Gly Ala Gly Ala Ala Ala Phe Pro Ala Leu Val Met Val Val Val
            115                 120                 125

Ala Arg Tyr Ile Pro Lys Glu Asn Arg Gly Lys Ala Phe Gly Leu Ile
    130                 135                 140

Gly Ser Ile Val Ala Met Gly Glu Gly Val Gly Pro Ala Ile Gly Gly
145                 150                 155                 160

Met Ile Ala His Tyr Ile His Trp Ser Tyr Leu Leu Leu Ile Pro Ile
                165                 170                 175

Ile Thr Ile Ile Thr Val Pro Phe Leu Met Lys Leu Leu Lys Lys Glu
            180                 185                 190

Val Arg Ile Lys Gly His Phe Gly Ser Lys Gly Ile Ile Leu Met Ser
    195                 200                 205

Val Gly Ile Val Phe Phe Met Leu Phe Thr Thr Ser Tyr Ser Ile Ser
    210                 215                 220

Phe Leu Ile Val Ser Val Leu Ser Phe Leu Ile Phe Val Lys His Ile
225                 230                 235                 240

Arg Lys Val Thr Asp Pro Phe Val Asp Pro Gly Leu Gly Lys Asn Ile
                245                 250                 255

Pro Phe Met Ile Gly Val Leu Cys Gly Gly Ile Ile Phe Gly Thr Val
```

-continued

```
                260                  265                   270
Ala Gly Phe Val Ser Met Val Pro Tyr Met Met Lys Asp Val His Gln
            275              280              285

Leu Ser Thr Ala Glu Ile Gly Ser Val Ile Ile Phe Pro Gly Thr Met
            290              295              300

Ser Val Ile Ile Phe Gly Tyr Ile Gly Gly Ile Leu Val Asp Arg Arg
305                      310              315                  320

Val Pro Leu Tyr Ala Leu Asn Ile Gly Val Thr Phe Leu Ser Val Ser
                    325              330              335

Phe Leu Thr Ala Ser Phe Leu Leu Glu Thr Thr Ser Trp Phe Met Thr
                340              345              350

Ile Ile Ile Val Phe Val Leu Gly Gly Leu Ser Phe Thr Lys Thr Val
            355              360              365

Ile Ser Thr Ile Val Ser Ser Leu Lys Gln Gln Glu Ala Gly Ala
    370              375              380

Gly Met Ser Leu Leu Asn Phe Thr Ser Leu Leu Ser Glu Gly Thr Gly
385                  390              395                  400

Ile Ala Ile Val Gly Gly Leu Leu Ser Ile Pro Leu Leu Asp Pro Arg
            405              410              415

Leu Leu Pro Met Glu Val Asp Gln Ser Thr Tyr Leu Tyr Ser Asn Leu
            420              425              430

Leu Leu Leu Phe Ser Gly Ile Ile Val Ile Ser Trp Leu Val Thr Leu
            435              440              445

Asn Leu Tyr Lys His Ser Gln Arg Asp Phe
    450              455
```

METHOD OF USING A GENE CONFERRING RESISTANCE TO 4,5-DIHYDROXY-2-CYCLOPENTEN-1-ONE (DHCP) AND IDENTIFYING INHIBITORS OF A POLYPEPTIDE ENCODED BY THE GENE

The patent application is a divisional application of application Ser. No. 09/805,681, filed Mar. 14, 2001 now abandoned, which claims the benefit of U.S. provisional Application No. 60/228,727, filed Aug. 29, 2000, hereby incorporated by reference.

BACKGROUND OF THE INVENTION

In spite of the number of antibiotics available against a variety of bacteria, due to emergence of multiple drug resistant strains, the search for never and more effective antibacterial compounds has continued. 4,5-dihydroxy-2-cyclopenten-1-one (DHCP) (see FIG. 1) is a compound having antibacterial activity against a variety of gram-positive and -negative bacteria, such as *Escherichia coli, Bacillu, Salmonella, Staphylococcus* etc. The process for manufacture and the propeties of DHCP have been patented (Koyama et al. 1999). It is prepared by the heat-treatment of uronic acid or its derivatives, wherein uronic acid is galacturonic acid, glucuronic acid, mannuronic acid, or iduronic acid. It is also produced from roasted or parched vegetables, fruits, cereals, mushrooms, sea algae, cortex, or cartilage. It has been demonstrated that this compound induces cancer cell differentiation and apoptosis. It has potential application as therapeutic or preventative agent against cancer and also as an antibacterial agent in antiseptics, dentrifices, cosmetics, and bathing agaents (Koyama et al. 1999).

We have isolated a multicopy suppressor from an *E. coli* genomic library for the DHCP toxicity. The putative protein encoded by this gene showed high homology to known efflux proteins conferring resistance to a number of antibiotics including chloramphenicol, bicyclomycin, and tetracycline. The gene was mapped at 37.5 min on the *E. coli* chromosome. It is designated as dep for DHCP-efflux protein. However, the Dep protein does not confer cross-resistance to any of the antibiotics tested.

BRIEF DESCRIPTION OF THE INVENTION

The provisional application describes the cloning of a gene encoding a transmembrane protein from *E. coli*. This protein, when expressed from a multi-copy plasmid, functions to transport 4,5-dihydroxy-2-cyclopenten-1-one (DHCP) out of the cell.

DHCP and functionally equivalent compounds are represented by the formulas [I] and [II] and include optically active compounds thereof. In Formula I, $R^1$ and $R^2$ are the same or different and each of them is hydrogen, a straight or branched alkyl group, a straight or branched alkenyl group, an aromatic group, an aromatic-aliphatic group, with the proviso that $R^1$=a benzyl group and $R^2$=H is excluded. See References 3 and 4. $R^3$-$R^6$ are independently hydrogen or an alkyl group, preferably a lower alkyl group such as a $C_1$-$C_6$ alkyl.

In Formula II, $R^1$ and $R^2$ are the same or different and each of them is hydrogen, a straight or branched alkyl group, a straight or branched alkenyl group, an aromatic group, an aromatic-aliphatic group, with the proviso that the case where $R^1$=$R^2$=$CH_3$ is excluded.

See References 5 and 6. $R^3$-$R^6$ are independently hydrogen or an alkyl group, preferably a lower alkyl group such as a $C_1$-$C_6$ alkyl.

DHCP is shown to possess anti-bacterial activity; it inhibits cell growth at a concentration of 350 .mu.M or higher. At lower concentrations, it causes cells to elongate and grow poorly. To determine if *E. coli* is naturally resistant to DHCP, a library of *E. coli* genomic DNA fragments was transformed into strain JM83 and grown on agar plates containing 400 .mu.M DHCP. Colonies that were capable of growing on this medium were isolated. DNA was isolated from these colonies to identify and sequence the cloned genomic fragment that specified resistance. Four genes were found in the fragment that conferred resistance. Inactivation of various combinations of these four genes led to the conclusion that ORF389 was responsible for conferring resistance. This was confirmed by cloning ORF389 by itself into pUC19 (a multicopy plasmid) and transforming strain JM83. The resultant cells were resistant to DHCP.

Comparison of the nucleotide sequence of ORF389 with the *E. coli* gene database showed that it was similar to known efflux proteins involved in conferring resistance to chloramphenicol and other antibiotics. Further analysis of the predicted structure of the protein encoded by ORF389 suggested that it was a membrane protein; it possesses multiple transmembrane domains and shares structural similarity with the aforementioned chloramphenicol efflux polypeptides.

To determine if ORF389 was capable of conferring resistance to other antibiotics such as chloramphenicol, spectinomycin, and tetracycline, the transformed JM83 cells containing the pUC19/ORF389 plasmid were plated on media containing these antibiotics. The presence of ORF389 failed to confer resistance to any antibiotic other than DHCP, suggesting that the efflux activity of the Dep protein is specific for DHCP.

It is important to note that ORF389 confers resistance to DHCP only when it is present in multiple copies in the cell. The gene is naturally found in the genome of *E. coli* cells, but it is present in single copy. Such cells are susceptible to the antimicrobial activity of DHCP. When ORF389 is cloned into pUC19 and introduced into JM83 cells, it is present in multiple copies (up to several hundred copies of the gene per cell), since pUC19 is maintained in up to several hundred copies per cell. Only when the gene dosage is increased, is resistance to DHCP found. The mechanism of resistance is simply increased efflux activity arising from the increased expression of the efflux protein in the transformed cells.

It should be noted that due to the degeneracy of the genetic code, the nucleotide sequence encoding an efflux protein that is responsible for conferring resistance to DHCP or a compound functionally equivalent to DHCP may vary from the nucleic acid sequence disclosed herein.

BRIEF DESCRIPTION OF THE DRAWINGS

FIG. 4 is a comparison of the amino acid sequence of the polypeptide encoded by dep (SEQ ID NO:3) with the proteins encoded by cmr (SEQ ID NO:4), cmrA (SEQ ID NO:5), cml (SEQ ID NO:6), cmx (SEQ ID NO:7), cmlv (SEQ ID NO:8), bcr (SEQ ID NO:9), bmr3 (SEQ ID NO: 10), yjcC (SEQ ID NO:11), and tet (SEQ ID NO: 12).

FIG. 6 is a nucleotide sequence (SEQ ID NO: 1) showing the DNA sequence of a region of the E. coli genome containing the sequence of the dep gene.

FIG. 7 is a nucleotide sequence (SEQ ID NO: 2) showing the isolated DNA sequence of the dep gene.

ADDITIONAL DESCRIPTION OF THE INVENTION

Mode of Action

DHCP is a compound that exhibits antimicrobial and anti-tumor activity. It is made by heating various uronic acids (e.g., glucuronic acid, galacturonic acid, mannuronic acid). The inventors have cloned a gene from E. coli that encodes a protein which is capable of transporting DHCP out of the cell. This transport protein shows sequence similarity with known efflux proteins that function to transport antibiotics such as chloramphenicol out of the cell. It has been shown that organisms which overexpress the transport protein become resistant to DHCP, probably because they are able to efficiently transport DHCP. Overexpression of the transport protein arises from the presence of multiple copies of the gene, rather than increased expression from the endogenous gene in E. coli. In other words, all E. coli possess a single copy of the transport gene. However, the level of transport protein expression from a single copy of the gene is insufficient to confer resistance to DHCP. The inventors have cloned the gene into a high copy number plasmid, pUC19, which is maintained in E. coli cells at 200-500 copies per cell. Thus, transformed E. coli containing this plasmid construct will possess 200-500 copies of the transport gene, and protein expression from multiple copies is greater than from a single copy. These transformed cells are resistant to DHCP.

The general mode of action of DHCP requires that it enter the target cell. Resistance to DHCP can occur if DHCP is transported out of the cell as fast as or faster than it enters the cell. Given that, the concentration of DHCP within the cell can never accumulate to a toxic dose and the cell is resistant to the antimicrobial effects of the compound. Apparently, the transport protein encoded by gene disclosed does not transport DHCP very efficiently, or the amount of transport protein expressed from the endogenous gene is very low. In either case, the presence of more transport protein (arising from many copies of the gene) will result in more efficient transfer of DHCP out of the cell.

Applications

An important application of the gene of the invention will be its use in studies to identify inhibitors of efflux activity. Such inhibitory compounds will function to block the transport activity. Thus a microbe or a tumor cell that is resistant to DHCP can be made to be more sensitive to the compound by preventing the resistant cell from transporting the compound back out. It is also conceivable that inhibitors of the transport gene of the invention may also be active in blocking transport of other efflux proteins such as the efflux proteins that transport chloramphenicol, or the P glycoprotein family of multiple drug resistant proteins. The P glycoproteins are expressed in many tumor cells, making these tumors resistant to chemotherapy agents. Abstracts regarding studies of P glycoproteins are referenced above.

DETAILED DESCRIPTION OF THE DRAWINGS

Figure 1:
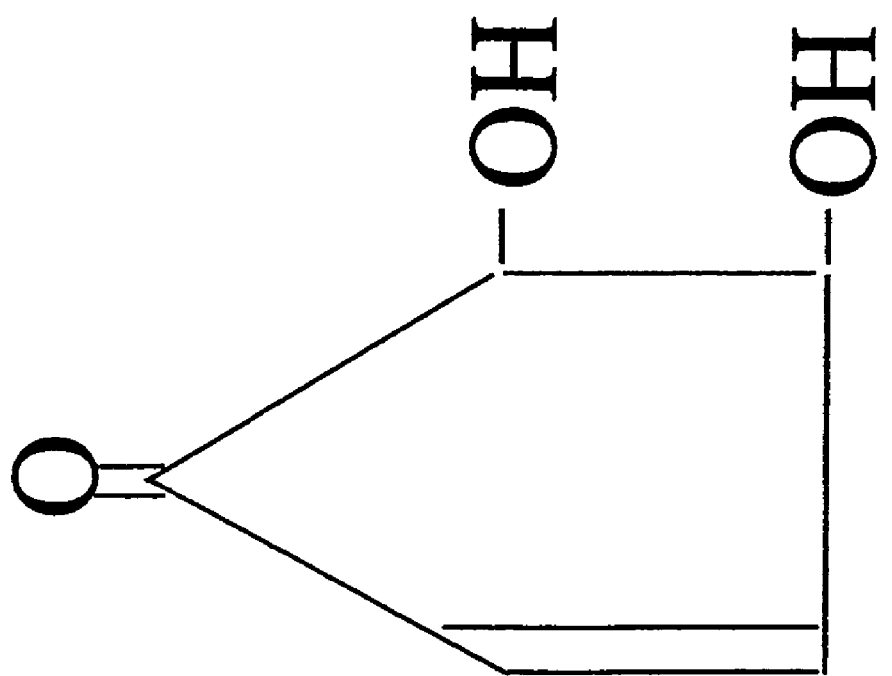
FIG. 1 is the chemical structure of 4,5-dihydroxy-2-cyclopenten-1-one (DHCP).

FIG. 1 is the chemical structure of 4,5-dihydroxy-2-cyclopenten-1-one (DHCP).

Figure 2:
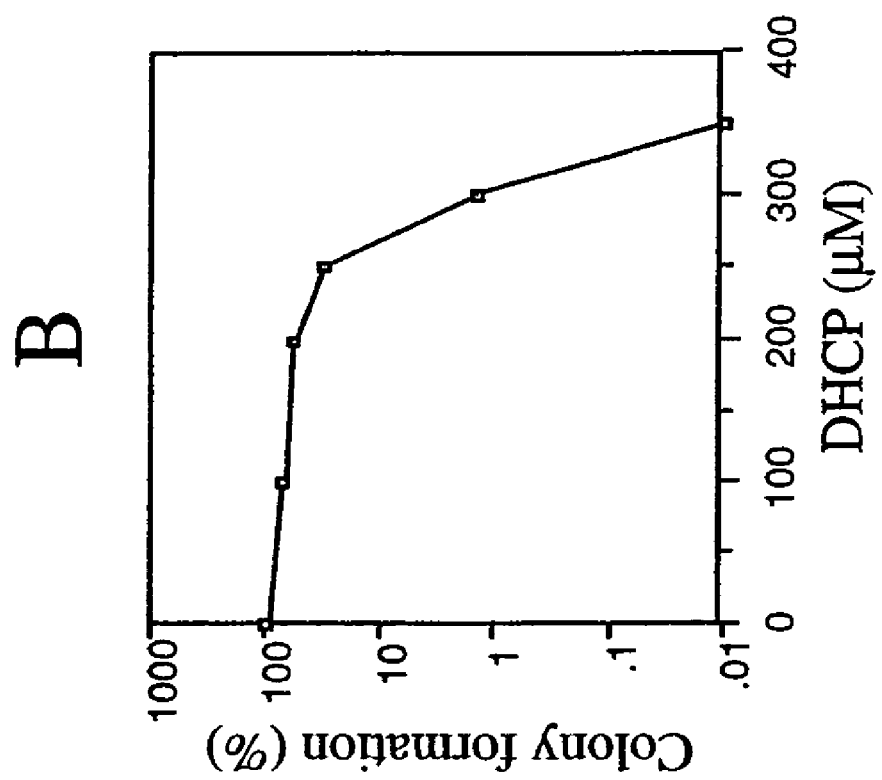
FIG. 2A is a graphical representation of the effect of DHCP concentration on the growth of *E. coli*.
FIG. 2B is a graphical representation of the effect of DHCP concentration on the survival of *E. coli*.
Figure 2:
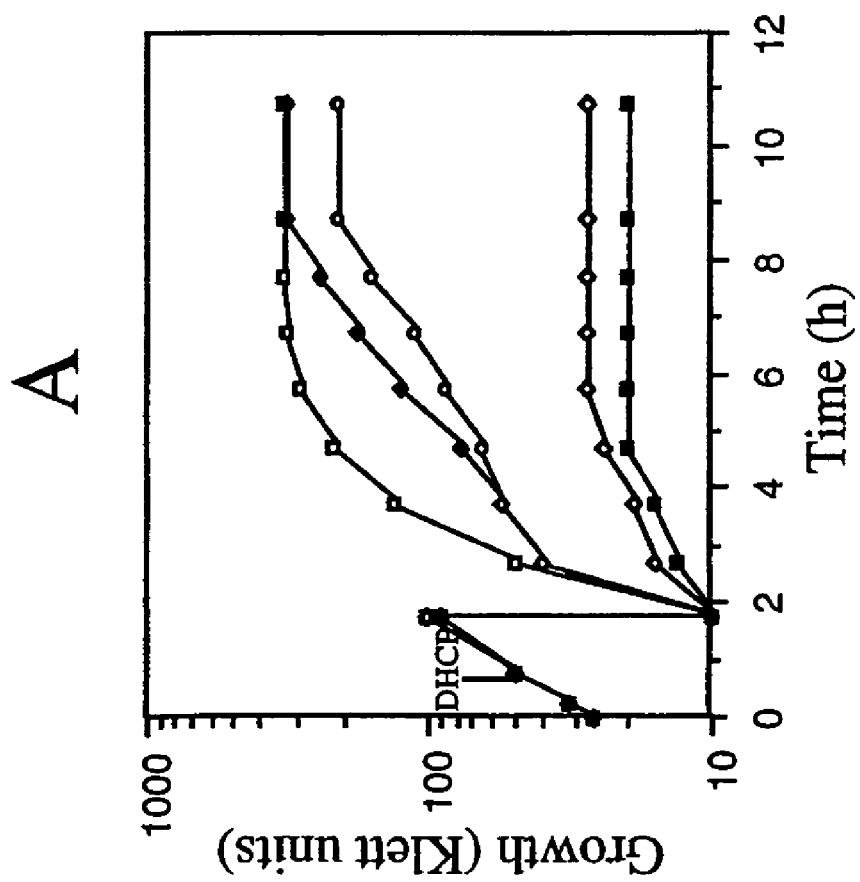

FIG. 2 Effect of DHCP concentrations on the growth of E. coli.

A. The JM83 cells were grown in LB medium up to Klett unit of 50 and DHCP was added at various concentrations (0-400 mu.M). After the growth reached to Klett unit of 90-100, cells were diluted with medium containing respective concentrations of DHCP and growth was further monitored. DHCP concentration: 0 . mu.M, open squares; 50 . mu.M, closed diamonds; 100 .mu.M, open circles; 250 . mu.M, open diamonds; 400 . mu.M closed squares. [0023] B. Overnight grown cells of E. coli JM83 were diluted appropriately and plated on LB plates containing different concentrations of DHCP (0-350 . mu.M). The number of colonies on the plate without DHCP was taken as 100% and the other numbers were expressed as relative percentages.

Figure 3:
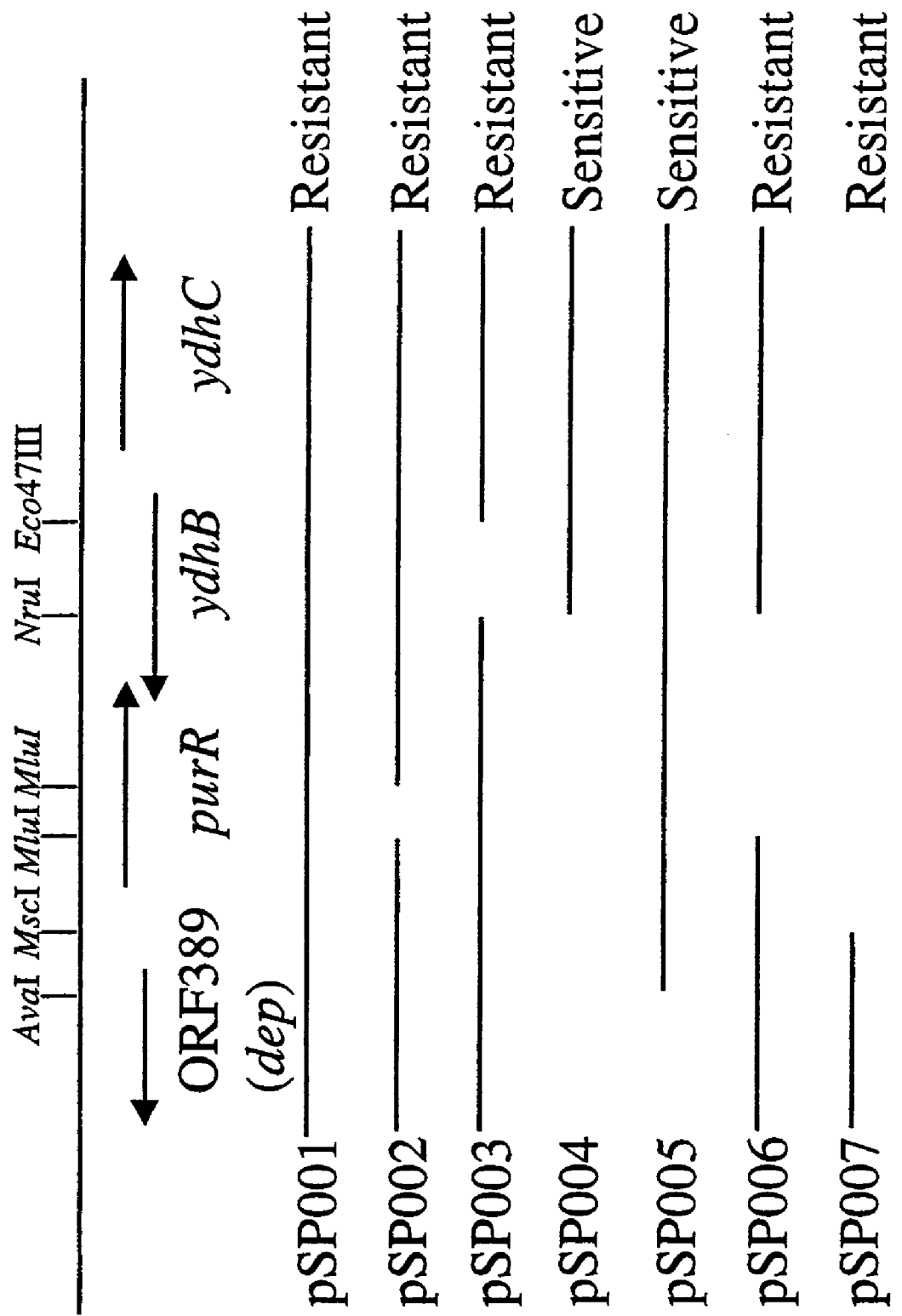
FIG. 3 is a restriction mapping of the plasmid pSP001 showing the DNA fragments conferring resistance to DHCP.

FIG. 3 Restriction mapping of the plasmid pSP001 conferring resistance to DHCP. Four ORFs comprising the DNA fragment (5.2 kb) conferring resistance to DHCP and the flanking ORFs are shown. The orientation of each ORF is marked with an arrow. The restriction enzyme sites are also shown. The ORFs are not drawn to scale. The plasmid pSP001 containing the DNA fragment conferring resistance to DHCP was digested with restriction enzymes to disrupt each of four ORFs, religated and transformed into JM83 cells. The transformants were then examined for their sensitivity to DHCP (400 . mu.M). The enzymes used for digestion were: for purR: MluI for ydhB; NruI-Eco47III, for ORF389, purR, and ydhB: NruI and SmaI, for ORF389: AvaI and for purR and ydhB: MluI and NruI. For construction of plasmid with ORF389 (dep), the plasmid pSP001 was digested with SmaI and MscI, the fragment was purified and cloned into pUC19 to yield plasmid pSP007.

Figure 4:
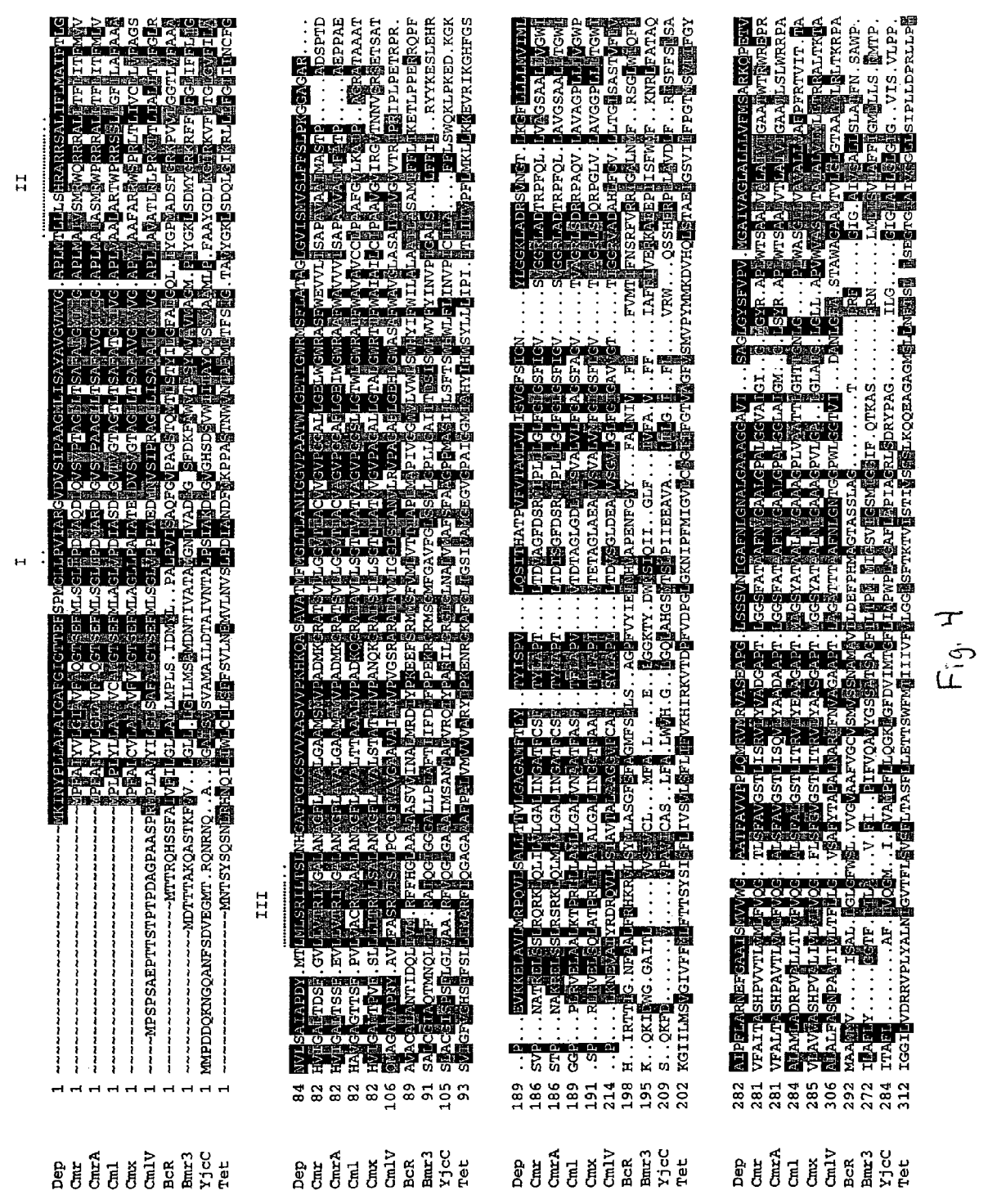

FIG. 4 The sequence homology between Dep, Cmr, CmrA, Cmx, CmlY, BcR, Bmr3, YjcC and Tet. Identical and similar sequences are marked with black and gray boxes, respectively. The consensus sequences for transmembrane proteins are marked with dotted lines and are represented as I, II, and III stretches.

Figure 5:
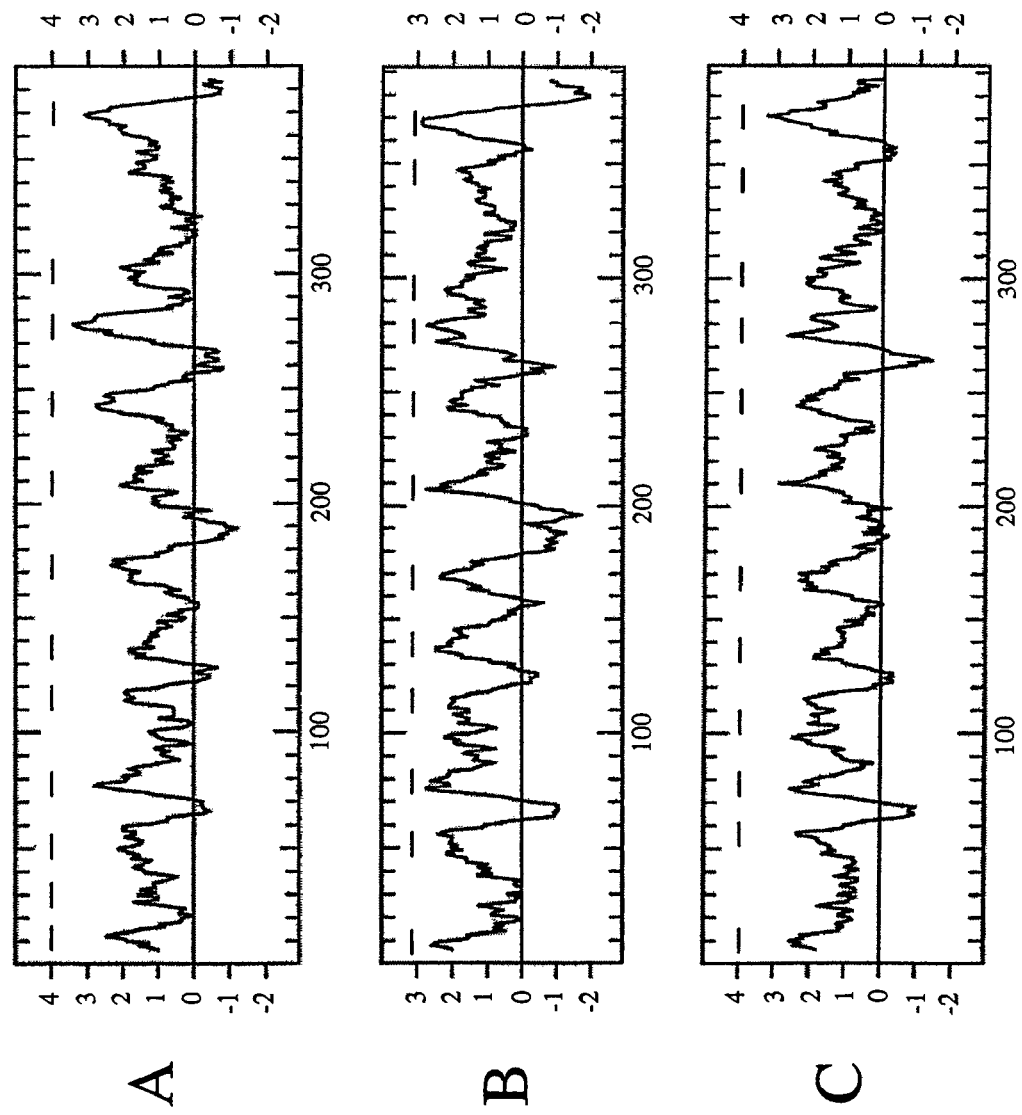
FIG. 5 is a comparison of the hydropathic profiles of the putative proteins encoded by dep, cmr, and cml.

FIG. 5 Hydropathic profiles of Dep (A), Cmr from *Rhodococcus faciens* (B) (6) and Cml from *Streptomyces lividans* (C) (8). Horizontal bars indicate predicted transmembrane regions.

FIG. 6 is a nucleotide sequence showing the DNA sequence of a region of the E. coli genome containing the sequence of the dep gene. This region of the E. coli genome is available at Accession No. AE000261 U00096. The sequence shown is that of nucleotides 4381-8280. The dep gene is encoded by nucleotides 4627-5838. The dep sequence is shown in brackets.

FIG. 7 is a nucleotide sequence showing the isolated DNA sequence of the dep gene. The plasmid pSP007 was confirmed to contain the dep gene by obtaining DNA sequence data from one end of the 1.7 kb insert. Sequence data obtained in this manner matched the first.

DETAILED DESCRIPTION OF EXPERIMENTAL WORK

Effect of DHCP on the Growth of *E. coli*

The *E. coli* wild-type strain JM83 [F.sup.-ara.DELTA. (lac-proAB) rpsL(st.sup.r)](Yanisch-Perron et al., 1985) was grown in Luria broth (LB). Media were supplemented with ampicillin (final concentration of 50 . mu.g/ml) whenever required. To check the effect of DHCP on the growth of *E. coli*, cells grown overnight in LB medium were diluted into fresh LB medium. After the growth reached to the Klett unit of 50, DHCP was added at various concentrations (0-400 . mu.M) and growth was further monitored. After it reached to the Klett unit of 90-100, it was diluted I O-fold into media containing respective concentrations of DHCP. FIG. 2A shows the effect of different concentrations of DHCP on *E. coli*. The growth was slowed after 3 h of incubation in the presence of 50 . mu.M DHCP, but it reached the maximum density after 8 h, similar to that without DHCP. The cells grew more slowly after 3 h incubation with 100 .mu.M of DHCP and the maximum cell density was lower than that without DHCP. In the presence of 250 . mu.M DHCP, growth was severely impaired after 3 h of incubation and cells stopped growing after 5 h. In the presence of 400 . mu.M DHCP, cell growth stopped after 4 h of incubation. Microscopic examination of the cells grown with 250 . mu.M DHCP for 8 h showed that the cells were elongated forming filaments, which are approximately 15-fold longer than the control cells. DAPI (diamidino phenylindole) (Hiraga et al., 1989) staining of these cells showed that the chromosomal condensation of the cells might be impaired by DHCP (data not shown).

To check the colony formation ability of *E. coli* at various concentrations of DHCP, cells grown overnight in LB medium were diluted appropriately and plated on LB plates containing DHCP (0-350 . mu.M). After incubation at 37. degree. C., the number of colonies on each plate were counted. The number of colonies on the control plate without DHCP was taken as 100% and the other numbers were expressed as relative percentages (FIG. 2B). In the presence of 300 .mu.M DHCP, 100-fold decrease in the colony numbers was observed. When 1.times.10.sup.4 cells were plated on LB medium containing 350 . mu.M DHCP, no colonies were obtained.

Screening of an *E. coli* Genomic Library for Genes Conferring Resistance to DHCP In order to examine if *E. coli* contains a gene(s) that confers resistance to DHCP, the *E. coli* genomic library was screened. The construction of *E. coli* genomic library was described previously (Lu and Inouye, 1998). The partially digested Sau3AI chromosomal DNA fragments from *E. coli* JM83 were cloned into the BamHI site of pUC19. The JM83 cells were transformed with the genomic library. Transformants were isolated for their ability to grow on. DHCP (400 .mu.M) containing LB plates at 37.degree. C. Plasmid DNA was isolated from the resistant colonies, purified and retransformed into JM83 cells to confirm its ability to confer resistance to DHCP. The plasmid was designated as pSP001 and was found to contain a 5.2-kb DNA fragment. This fragment was sequenced from both ends using Sequenase and BLAST search was carried out for the analysis of homology of this fragment with the entire *E. coli* genome. It was found that this DNA fragment is located at 37.5 min on the *E. coli* chromosome and contains four ORFs (FIG. 3): ORF389, purR encoding purine synthesis repressor, ydhB encoding a homologue of the cyn operon transcriptional activator and ydhC encoding a homologue of bicyclomycin resistance protein (Berlyn et al., 1996).

To determine which gene is responsible for conferring resistance to DHCP, several deletion constructs were prepared as shown in FIG. 3. Disruption of purR, ydhB and both purR and ydhB had no effect on the resistance to DHCP (constructs pSP002, pSP003 and pSP006, respectively). However, disruption of ORF389 with purR and ydhB (pSP004) as well as disruption of ORF389 alone (pSP005) resulted in loss of DHCP resistance. We thus cloned ORF389 separately in pUC19 (pSP007), transformed the resultant plasmid in JM83 and checked sensitivity to DHCP. This plasmid conferred resistance to DHCP. These results clearly demonstrate that ORF389 is responsible for resistance to DHCP when cloned in a multicopy plasmid and further work was carried out using the plasmid pSP007. The ORF389 was named as dep-DHCP efflux protein (see below).

Homology Analysis of ORF389 with Other Genes Conferring Drug Resistance

Using BLAST-homology search computer program, we carried out a homology search for the putative protein encoded by dep. FIG. 4 shows nine proteins showing significantly high homology with Dep. Half of these proteins confer resistance to chloramphenicol. The proteins showing the highest degree of homology include: Cmr from *Rhodococcus-fasciens* (Desomer et al., 1992), CmrA from *R. erythropolis* (Nagy et al., 1997), Cml from *Streptomyces lividans* 1326 (Dittrich et al., 1991), Cmx from *Corynebacterium striatum*, (Accession no. U72639), and CmlV from *S. venezuelae* ISP5230 (Mosher.et al., 1995). As seen from FIG. 4, Dep has the highest degree of homology with Cmr, product of chloramphenicol resistant gene (cmr) as compared to other proteins. Cmr protein was shown to contain three consensus sequences defined by Rouch et al. (1990) for transmembrane proteins. These sequences are at similar positions with respect to the predicted transmembrane domains. These are marked in FIG. 6 with dotted lines and are designated as I, II, III. In case of Dep, the first stretch (I) comprising of LP is completely homologous with the stretch defined by these authors. The second stretch (II) shows 50% similarity with that of Cmr protein and the third stretch (III) is homologous between these two proteins except for one residue. According to the model proposed by Rouch et al. (1990), the stretches I and III are located on the outside of the cytoplasmic membrane and the stretch II is located on the inside of the membrane. The positions of the membrane loops for the putative protein encoded by qacA were ascertained by inspecting the antigenic index profile and turn prediction. Such regions have a high antigenic index and turn probability (Rouch et al., 1990).

In addition to homology in the primary sequences, the hydropathic profile of Dep (FIG. 5A) is significantly similar to those of Cmr of *R. faciens* (Desomer et al., 1992) (FIG. 5B) and Cml of *S. lividans* (Dittrich et al., 1991) (FIG. 5C). Dep is predominantly hydrophobic and probably contains 12 predicted transmembrane .alpha.-helices (FIG. 5A).

The other proteins homologous to Dep include BcR (bicyclomycin-resistance protein) from *E. coli* (Bentley et al., 1993), Bmr3 from *B. subtilis* involved in the multiple drug efflux pump conferring resistance to puromycin, tosufloxacin, norfloxacin (Ohki and Murata, 1997), Tet from *Staphylococcus hyicus* conferring tetracycline resistance (Schwarz et al., 1992) and YjcC conferring tetracenomycin-resistance (Accession no. D90826) (FIG. 4). All of these are efflux proteins, which is one of the most common mechanisms for drug resistance. We speculate that dep encodes a putative efflux protein that forms a cytoplasmic channel specific for DHCP. The homologies are more prominent towards the N-terminal end of the proteins, which also is a common feature for efflux proteins (Desomer et al., 1992).

Measurement of Minimum Inhibitory Concentrations for Cells Harboring PUC19 and pSP007

Since Dep shows homology to efflux proteins for multiple drug resistance, we checked if it confers resistance to other antibiotics as well. The *E. coli* wild-type cells harboring pUC19 or pSP007 plasmid were grown overnight in LB medium containing ampicillin. The cells were diluted 10- and 1000-times, and 5 mu.l of each dilution (corresponding to $3.5 \times 10^5$ cells and $3.5 \times 10^3$ cells, respectively) was spotted on LB plates containing serial dilutions of kanamycin, chloramphenicol, spectinomycin, tetracycline and DHCP. Plates were incubated at 37.degree. C. for 20 h. As seen from Table 1, pSP007 did not confer significant cross-resistance to any of the antibiotics tested. The MIC values for cells harboring pUC19 and pSP007 were same for spectinomycin, chloramphenicol and tetracycline. The MIC value was two times higher for kanamycin for the cells harboring pSP007 than the cells with pUC19. The MIC value for DHCP on the other hand was 8 times higher for the cells-harboring pSP007 than that for the cells with pUC19. It is interesting that Dep did not confer resistance to chloramphenicol, in spite of the high homology to cmr.

TABLE 1

Minimum inhibitory concentrations (MICs) of various antibiotics for *E. coli* JM83 cells harboring pUC19 and pSP007.

|  | kanamycin | spectino-mycin | MICs (µg/ml) chloramphenicol | tetra-cycline | DHCP |
|---|---|---|---|---|---|
| cells with pUC19 | 25 | 12.5 | 6.25 | 3.125 | 25 |
| cells with pSP007 | 50 | 12.5 | 6.25 | 3.125 | 200 |

MICs for both dilutions of the cells ($3.5 \times 10^5$ and $3.5 \times 10^3$ cells) were the same.

MICs for both dilutions of the cells ($3.5 \times 10^5$ and $3.5 \times 10^3$) were the same.

PRIOR ART REFERENCES

U.S. Pat. No. 6,087,401 to Koyama, et al. Cyclopentones, process for preparing same, and the use thereof.

This patent discloses a method of manufacturing 4,5-dihydroxy-2-cyclopenten-1-one (DHCP). It also describes the antibacterial activity of DHCP.

In contrast, the invention disclosed in the present provisional application relates to a gene, dep, that, when present in multiple copies in bacterial cells, confers resistance to the antibacterial activity of DHCP, thus rendering the bacteria resistant to killing by DHCP. The present application also describes the protein encoded by the dep gene.

European Patent EP 0 941 981 A1 to Koyama, et al. Cyclopentones, process for preparing same, and the use thereof.

This patent application relates to essentially the same subject matter as that described in U.S. Pat. No. 6,087,401 to Koyama, et al. U.S. Pat. No. 6,111,145 to Kobayashi et al. Cyclopentenone derivative.

This patent relates to functionally equivalent ether derivatives of DHCP and discloses the biological activity of these derivatives.

European Patent Publication EP 1 000 923 A1 to Kobayashi et al. Cyclopentenone derivatives.

This patent application relates to essentially the same subject matter as that described in U.S. Pat. No. 6,111,145 to Kobayashi et al.

U.S. Pat. No. 6,136,854 to Koyama et al. Cyclopentenone derivative.

This patent relates to functionally equivalent ester derivatives of DHCP and discloses the biological activity of these derivatives.

European Patent Publication EP 0 976 717 A1 to Koyama et al. Cyclopentenone derivatives.

This patent application relates to essentially the same subject matter as that described in U.S. Pat. No. 6,136,854 to Koyama et al.

Clinical significance of P-glycoprotein expression and function for response to induction chemotherapy, relapse rate and overall survival in acute leukemia. C. Wuchter, et al. Haematologica 85(7):711-21 (2000).

In acute leukemia, a multidrug-resistance (MDR) phenotype mediated by P-glycoprotein (P-gp) contributes to chemotherapy failure. This study investigated whether P-gp expression levels or functional P-gp activity was a better predictor of response to induction chemotherapy, relapse rate and overall survival in acute leukemia. The data demonstrated that the functional rhodamine-123-(rh123)-efflux assay was preferred over P-gp expression analysis by monoclonal antibodies in acute leukemia.

Increased drug delivery to the brain by P-glycoprotein inhibition. A. J. Sadeque, et al. Clinical Pharmacology & Therapeutics 68(3):231-7 (2000).

In vitro studies had demonstrated that the antidiarrheal drug loperamide is a substrate for the efflux membrane transporter P-glycoprotein. Although loperamide is a potent opiate drug, it does not opioid central nervous system effects, such as respiratory depression, when given to patients at usual doses. This study tested the hypothesis that inhibition of P-glycoprotein with quinidine would increase the entry of loperamide into the central nervous system, thus causing respiratory depression. The results demonstrated that although loperamide produced no respiratory depression when used alone, respiratory depression was seen when loperamide was administered with quinidine.

Expression of the multidrug-resistance-associated protein in myelodysplastic syndromes. S. Poulain, et al. British Journal of Haematology 110(3):591-8 (2000).

In myelodysplastic syndromes (MDS), P-glycoprotein (P-gp) expression is associated with drug resistance, while the clinical significance of the multidrug resistance-associated protein (MRP1) is unclear. In this study of bone marrow from patients with MDS, expression of MRP1 was correlated with disease stage in MDS. With respect to P-gp, discordant expression/function of MRP1 was found in some cases, suggesting the existence of nonfunctional transport proteins in MDS. MRP1 expression did not appear to be a prognostic factor in MDS.

Soft tissue leiomyosarcomas and malignant gastrointestinal stromal tumors: differences in clinical outcome and expression of multidrug resistance proteins. B. E. Plaat, et al. Journal of Clinical Oncology 18(18):321.1-20 (2000).

In this study, parameters associated with multidrug resistance (MDR) were compared between soft tissue leiomyosarcomas (LMS) and malignant gastrointestinal stromal tumors (GIST). Immunohistochemistry was used to detect P-glycoprotein (P-gp), multidrug resistance protein (MRP(1)), lung resistance protein (LRP), and c-kit. The results demonstrate that LMS patients have better survival rates compared to GIST patients, and the pattern of metastasis differs between the two patient groups. The expression of the MDR proteins tested is less pronounced in LMS than in GIST.

Quorun sensing in *Escherichia coli, Salmonella typhimurium*, and *Vibrio harveyi*: A new family of genes responsible for autoinducer production. M. G. Surette, et al. Proc. Natl. Acad. Sci. 96:1639-44 (1999).

In bacteria, the regulation of gene expression in response to changes in cell density, called quorum sensing, is dependent on hormone-like molecules known as autoinducers that are produced by the bacteria and accumulate in the external environment as the bacterial cell population increases. The marine bacterium *Vibrio harveyi* has been shown to have two parallel quorum sensing systems, each composed of a sensor-autoinducer pair. The two different autoinducers belonging to each system have been termed autoinducer 1 (AI-1) and autoinducer 2 (AI-2). The identification and analysis of the genes responsible for AI-2 production in *E. coli, S. typhimurium*, and *V. harveyi* is reported.

Quorum sensing in *Vibrio fischeri*: Probing autoinducer-LuxR interactions with autoinducer analogs. A. L. Schaefer, et al. Journal of Bacteriology 178:2897-2901 (1996).

In *Vibrio fischeri*, luminescence genes are activated by the transcription factor LuxR in combination with a diffusible signal compound known as the autoinducer. This study analyzed the ability of a number of autoinducer analogs to interact with LuxR.

Regulation of quorum sensing in *Vibrio harveyi* by LuxO and Sigma-54. B. N. Lilley and B. L. Bassler. Molecular Microbiology 36(4):940-954 (2000).

The bioluminescent marine bacterium *Vibrio* harveyi controls light production (lux) by a quorum-sensing circuit. This study demonstrates that the response regulator protein LuxO functions as an activator protein via interaction with the alternative sigma factor, .sigma..sup.54. Since LuxO is responsible for repression of the luciferase structural operon (luxCDABEGH), these results suggest that LuxO, together with .sigma..sup.54, functions to activate a negative regulator of luminescence.

Bentley, J., Hyatt, L. S., Ainley, K., Parish, J. H., Herbert, R. B., and White, G. R. 1993. Cloning and sequence analysis of an *Escherichia coli* gene conferring bicyclomycin resistance. Gene 127:117-120.

Berlyn, M. K. B., Low, K. B., and Rudd. K. E. 1996. Linkage map of *Escherichia coli* K-12, Ed. 9. Pages 1715-1902. In Neidhardt, F. C., Curtiss III; R., Ingraham, J. L., Lin, E. C. C., et al. (ed) *Escherichia coli* and *Salmonella*. Cellular and Molecular Biology, Vol. 2, 2nd Ed., ASM Press, Washington D.C.

Desomer, J., Vereecke, D., Crespi, M., and Van Montagu, M. 1992. The plasmid-encoded chloramphenicol-resistance protein of *Rhodococcus fascians* is homologous to the transmembrane tetracycline efflux proteins. Mol. Microbiol. 6: 2377-2385.

17. Dittrich, W., Betzler, M., and Schrempf, H. 1991. An amplifiable and deletable chloramphenicol-resistance determinant of *Streptomyces lividans* 1326 encodes a putative transmembrane protein. Mol. Microbiol. 5:2789-2797.

Hiraga S., Niki, H., Ogura, T., Ichinose, C., Mori, H., Ezaki, B., and Jaffe, A. 1989. Chromosome partitioning in *Escherichia coli*: novel mutants producing anucleate cells. J. Bacteriol. 171:1496-505.

Koyama, N., Sagawa, H., Kobayashi, E., Enoki, T., Wu, H-K., Nishiyama, E., Ikai, K., and Kato, I. 1999. Cyclopentanones, process for preparing the same, and the use thereof. European Patent (EP 0941 981 A1, date of publication: Sep. 15, 1999).

Lu Q., and Inouye, M. 1998. The gene for 16S rRNA methyltransferase (ksga) functions as a multicopy suppressor for a cold-sensitive mutant of Era, an essential RAS-like GTP-binding protein in *Escherichia coli*. J. Bacteriol. 180: 5243-5246.

Mosher, R. H., Camp, D. J., Yang, K., Brown, M. P., Shawl, W. V., and Vining, L. C. 1995. Inactivation of chloramphenicol by O-phosphorylation. J. Biol. Chem. 270:27000-27006.

Nagy, I., Schoofs, G., Vanderleyden, J., and De Mot, R. 1997. Transposition of the IS21-related element IS1415 in *Rhodococcus erythropolis*. J. Bacteriol. 179:4635-4638.

Ohki, R., and Murata, M. 1997. bmr3, a third multidrug transporter gene of *Bacillus subtilis* J. Bacteriol. 179:1423-1427.

Rouch, D. A., Cram, D. S., DiBerardino, D., Littlejohn, T. G., and Skurray, R. A. 1990. Efflux-mediated antiseptic resistance gene qacA from *Staphylococcus aureus*: common ancestry with tetracycline- and sugar-transport proteins. Mol. Microbiol. 4:2051-2062.

Schwarz, S., Cardoso, M., and Wegener, H. C. 1992. Nucleotide sequence and phylogeny of the tet(L) tetracycline resistance determinant encoded by plasmid pSTE1 from *Staphylococcus hyicus*. Antimicrob. Agents Chemother. 36:580-588.

Yanisch-Perron, C., Vieira, J., and Messing, J. 1985. Improved M13 phage cloning vectors and host strains: Nucleotide sequences of the M13 mp18 and pUC19 vectors. Gene 33: 103-119.

All references cited herein are incorporated by reference.

---

We claim:

1. A method of conferring resistance to 4,5-dihydroxy-2-cyclopenten-1-one comprising:
   (a) transfecting bacteria with a vector comprising a gene encoding a protein comprising SEQ ID NO: 3, and
   (b) culturing the transfected bacteria in a medium containing 4,5-dihydroxy-2-cyclopenten-1-one, thereby obtaining bacteria resistant to 4,5-dihydroxy-2-cyclopenten-1-one.

2. A method of identifying a compound that inhibits efflux activity responsible for 4,5-dihydroxy-2-cyclopenten-1-one resistance comprising:
   (a) transfecting bacteria with a vector comprising a gene encoding a protein comprising SEQ ID NO: 3,
   (b) treating the bacteria with 4,5-dihydroxy-2-cyclopenten-1-one,
   (c) contacting the bacteria with one or more potential inhibitors of the protein of SEQ ID NO: 3, and
   (d) measuring bacterial growth and comparing a rate of growth of the bacteria in the presence and absence of one or more potential inhibitors of SEQ ID NO: 3.

* * * * *

UNITED STATES PATENT AND TRADEMARK OFFICE
CERTIFICATE OF CORRECTION

PATENT NO. : 7,476,526 B2 Page 1 of 1
APPLICATION NO. : 11/224538
DATED : January 13, 2009
INVENTOR(S) : Phadtare et al.

It is certified that error appears in the above-identified patent and that said Letters Patent is hereby corrected as shown below:

In Column 1
At line 34, please change "agaents" to --agents--.

In Column 5
At line 15, please change "I O-fold" to --10-fold--.

Signed and Sealed this

Twenty-third Day of June, 2009

JOHN DOLL
*Acting Director of the United States Patent and Trademark Office*